United States Patent
Wu et al.

(10) Patent No.: US 10,407,503 B2
(45) Date of Patent: Sep. 10, 2019

(54) FULLY HUMAN ANTIBODIES AND FRAGMENTS RECOGNIZING HUMAN C-MET

(71) Applicant: THE REGENTS OF THE UNIVERSITY OF CALIFORNIA, Oakland, CA (US)

(72) Inventors: Anna M. Wu, Sherman Oaks, CA (US); Keyu Li, Sunnyvale, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 482 days.

(21) Appl. No.: 14/647,954

(22) PCT Filed: Dec. 2, 2013

(86) PCT No.: PCT/US2013/072668
§ 371 (c)(1),
(2) Date: May 28, 2015

(87) PCT Pub. No.: WO2014/085821
PCT Pub. Date: Jun. 5, 2014

(65) Prior Publication Data
US 2015/0299326 A1    Oct. 22, 2015

Related U.S. Application Data

(60) Provisional application No. 61/732,153, filed on Nov. 30, 2012.

(51) Int. Cl.
| | | |
|---|---|---|
| *A61K 39/395* | (2006.01) | |
| *C07K 16/28* | (2006.01) | |
| *A61K 45/06* | (2006.01) | |
| *A61K 51/10* | (2006.01) | |
| *G01N 33/574* | (2006.01) | |
| *A61K 47/68* | (2017.01) | |
| *A61K 39/00* | (2006.01) | |

(52) U.S. Cl.
CPC ...... *C07K 16/2863* (2013.01); *A61K 39/3955* (2013.01); *A61K 45/06* (2013.01); *A61K 47/6849* (2017.08); *A61K 51/103* (2013.01); *G01N 33/57423* (2013.01); *A61K 2039/505* (2013.01); *C07K 2317/21* (2013.01); *C07K 2317/24* (2013.01); *C07K 2317/33* (2013.01); *C07K 2317/56* (2013.01); *C07K 2317/565* (2013.01); *C07K 2317/622* (2013.01); *C07K 2317/626* (2013.01); *C07K 2317/73* (2013.01); *C07K 2317/76* (2013.01); *C07K 2317/92* (2013.01); *G01N 2333/71* (2013.01); *G01N 2333/91205* (2013.01)

(58) Field of Classification Search
None
See application file for complete search history.

(56) References Cited

U.S. PATENT DOCUMENTS

| | | |
|---|---|---|
| 4,342,566 A | 8/1982 | Theofilopoulous |
| 4,676,980 A | 6/1987 | Segal |
| 4,816,567 A | 3/1989 | Cabilly |
| 5,545,806 A | 8/1996 | Lonberg |
| 5,545,807 A | 8/1996 | Surani |
| 5,569,825 A | 10/1996 | Lonberg |
| 5,625,126 A | 4/1997 | Lonberg |
| 5,633,425 A | 5/1997 | Lonberg |
| 5,661,016 A | 8/1997 | Lonberg |
| 5,750,373 A | 5/1998 | Garrard |
| 6,492,123 B1 | 12/2002 | Holliger |

FOREIGN PATENT DOCUMENTS

| | | |
|---|---|---|
| WO | WO 1993/006213 | 4/1993 |
| WO | WO 1994/029348 | 12/1994 |

OTHER PUBLICATIONS

Tockman et al, Cancer Research vol. 52 p. 2711s (1992) (Year: 1992).*
Janicke et al Fibrinolysis vol. 4 p. 69 (1990) (Year: 1990).*
Ezzell (J. NIH Res. 1995 7:46) (Year: 1995).*
Dimitrov mAbs vol. 2, p. 347 (2010) (Year: 2010).*
Strome et al., The Oncologist, 2007; 12:1084-95 (Year: 2007).*
Brand et al., Anticancer Res. 2006; 26:463-70 (Year: 2006).*
Spitler (Cancer Biotherapy, 1995, 10:1-3) (Year: 1995).*
X Liu et al, Trends in Molecular Medicine, 2009.
E M Rosen et al, JCB, 1994.
C Birchmeier et al, Trends in Cell Biology, 1998.
J Engelman et al, Science, 2007.
N Puri et al, Cancer Research, 2007.
S Berthou et al, Oncogene, 2004.
T Underiner et al, Anti-Cancer Agents in Medicinal Chemistry, 2010.
L R Perk et al, Eur J Nucl Med Mol Imaging, 2008.
E M Jagoda et al, JNM, 2012.
Kohler and Milstein, Nature, 256:495 (1975).
Jones et al., Nature, 321:522-525 (1986).
Riechmann et al., Nature, 332:323-327 (1988).
Verhoeyen et al., Science, 239:1534-1536 (1988).
Kozbor, J. Immunol. 133, 3001 (1984).
Brodeur, et al., Monoclonal Antibody Production Techniques and Applications, pp. 51-63 (Marcel Dekker, Inc., New York, 1987).
Jakobovits et al., Proc. Natl. Acad. Sci. USA 90, 2551-255 (1993).
Jakobovits et al., Nature 362, 255-258 (1993).
Mendez et al. (Nature Genetics 15: 146-156 (1997).
McCafferty et al., Nature 348, 552-553 (1990).
Johnson, Kevin S. and Chiswell, David J., Current Opinion in Structural Biology 3, 564-571 (1993).
Clackson et al., Nature 352, 624-628 (1991).
Marks et al., J. Mol. Biol. 222, 581-597 (1991).
Griffith et al., EMBO J. 12, 725-734 (1993).
Marks et al., Bio/Technol. 10, 779-783 (1992).
Waterhouse et al., Nucl. Acids Res. 21, 2265-2266 (1993).
Morimoto et al., J. Biochem. Biophys. Methods 24:107-117 (1992).
Brennan et al., Science 229:81 (1985).
Carter et al., Bio/Technology 10:163-167 (1992).

* cited by examiner

*Primary Examiner* — Sheela J. Huff
(74) *Attorney, Agent, or Firm* — Morgan, Lewis & Bockius LLP; Jeffry S. Mann; Louis T. Nguyen

(57) ABSTRACT

Human antibody fragments against c-Met have been identified through phage display technology. The high affinity and low immunogenicity make them very useful for both in vivo and in vitro applications. These novel human antibodies can greatly help the study of drug resistance in EGFR targeted therapies, and improve the diagnosis and treatment of cancer patients.

38 Claims, 19 Drawing Sheets

Specification includes a Sequence Listing.

Figure 1

SEQ ID NO:1
A12 heavy chain variable domain sequence
QVQLVQSGGGLVQPGGSLRLSCAASGFTFSSYAMSWVRQAPGKGLEWVS**AISGSGGSTYYAD
SVKGRFTISRDNSKNTLYLQMNSLRAEDTAVYYCAKSSSSWYRSYYFDY**WGQGTLVTVSS SEQ ID NO:2
C2 heavy chain variable domain
QVQLQESGGGLVQPGGSLRLSCAASGFTFSSYAMSWVRQAPGKGLEWVS**AISGSGGSTYYADS
VKGRFTISRDNSKNTLYLQMNSLRAEDTAVYYCASQHVGEQSRYFDY**WGQGTLVTVSS SEQ ID NO:3
E9 heavy chain variable domain sequence
QVQLQESGGGVVQPGRSLRLSCAASGFTFSSYGMHWVRQAPGKGLEWVS**AIGSSGGSTHDAD
TVKGRFTISRDNAKNSLYLQMNSLRAEDTAVYYCARDRARGFDY**WGQGTLVTVSS SEQ ID NO:4
F1 heavy chain variable domain sequence
QVQLVQSGAEVKKPGASVKVSCKASGYTFTDYYMHWVRQAPGEGLEWMG**WMNPNSGGTN
YAQKFQGRVTMTRDTSISTAYMELSRLRSDDTAVYYCARSHYWDS**WSPGTLVTVSS SEQ ID NO:5
F11 heavy chain variable domain sequence
QVQLQESGGGLLQPGGSLRLSCAASRFTFSNYAMSWVRQAPGKGLEWVS**AISGSGASTYYADS
VKGRFTISRDNSKNTLYLQMNSLRAEDTAVYYCSNLYGDYDY**WGQGTLVTVSS SEQ ID NO:6
G1 heavy chain variable domain sequence
QVQLQESGGGVVQPGGSLRLSCAASGFTFSSYSMNWVRQAPGKGLEWVS**SISSSSSYIYYADSV
KGRFTISRDNAKNSLYLQMNSLRAEDTAVYYCARDLPSDDYGDYDYYYYGMDV**WGQGTTVT
VSS SEQ ID NO:7
H2 heavy chain variable domain sequence
EVQLVESGGGLVQPGGSLRLSCAASGFTFSTYAMSWVRQAPGKGLEWVS**AISGSGGSTYYADS
VKGRFTISRDNSKNTLYLQMNSLRAEDTAVYYCAREGGKWYYGMDV**WGRGTLVTVSS SEQ ID NO:8
H5 heavy chain variable domain sequence
QVQLQESGGGLVQPGGSLRLSCAASGFTFSNYAMSWVRQAPGKGLEWVS**AISGSGGSTYYAD
SVKGRFTISRDNSKNTLYLQMNSLRAEDTAVYYCAKDRFRAAAY**WGQGTLVTVSS

Figure 2

SEQ ID NO:9
A12 light chain variable domain sequence
QSALTQDPAVSVALGQTVRITCRGDSLRNYYASWYQQKPGQAPVLVIYGKNNRPSGIPDRFSGS
FSGNTASLTITGAQAEDEADYYCNSRDSSANQMFGGGTKVTVLG

SEQ ID NO:10
C2 light chain variable domain sequence
DIVMTQSPSSLSASIGDRVTITCRASHSISSYVNWYQKKPGKAPNLLIYAASYLPRGVPSRFSGSG
LGTDFTLTISNLQPEDFATYYCQESYSTPYSFGQGTKVDIKR

SEQ ID NO:11
E9 light chain variable domain sequence
EIVLTQSPSTLSASIGDRVTITCRASQGISSYLAWYQQKPGKAPKLLIYGASSLQSGVPSRFSGRG
SGADFTLTISSLQPEDFATYYCQQLISYPLTFGGGTKVEIKR

SEQ ID NO:12
F1 light chain variable domain sequence
SALTQPASVSGSPGQSITISCTGTSGDVGGYNYVSWYQQHPGKAPKLMIYDVSNRPSGVSNRFS
GSKSGNTASLTISGLQAEDEADYYCTSYAGSRNLVFGGGTKLTVLG

SEQ ID NO:13
F11 light chain variable domain sequence
QSVLTQPASVSGSPGQSITISCTGTSSDVGGYNYVSWYQQHPGKAPKLMIYDVSNRPSGVSNRF
SGSKSGNTASLTISGLQAEDEADYYCSSYTSSSTLLFGGGTKLTVLG

SEQ ID NO:14
G1 light chain variable domain sequence
QSVLTQPPSASGTPGQRVTLFCSGSSSNIASNSVKWYQQPPQRAPKLLMFSDDQRPSGVPVRFSA
SKSGTSASLAISGLQSEDEADYYCAAWDDSLNAEVFGGGTKVTVLG

SEQ ID NO:15
H2 light chain variable domain sequence
SSELTQDPAVSVALGQTVRITCQGDSLRSYYTNWFQQKPGQAPLLVVYAKNKRPSGIPDRFSGS
GSGDTASLTITGAQAEDEADYYCNSRDSSGNYLFAAGTKLTVLG

SEQ ID NO:16
H5 light chain variable domain sequence
QSVLTQPPSVSAAPGQKVTISCTGSSSNIGAGYDVHWYQQLPGTAPKLLIYGNSNRPSGVPDRFS
GSKSGTSASLAISGLQSEDEADYYCAAWDDILNGEIFGGGTKVTVLG

Figure 3

SEQ ID NO:17
A12 cys-diabody sequence
QVQLVQSGGGLVQPGGSLRLSCAASGFTFSSYAMSWVRQAPGKGLEWVS**AISGSGGSTYYAD
SVKGRFTISRDNSKNTLYLQMNSLRAEDTAVYYCAKSSSSWYRSYYFDY**WGQGTLVTVSSGGG
GGSQSALTQDPAVSVALGQTVRITCRGDSLRNYYASWYQQKPGQAPVLVIYGKNNRPSGIPDR
FSGSFSGNTASLTITGAQAEDEADYYCNSRDSSANQMFGGGTKVTVLGAAAEQKLISEEDLNGA
AHHHHHHC

SEQ ID NO:18
C2 cys-diabody sequence
QVQLQESGGGLVQPGGSLRLSCAASGFTFSSYAMSWVRQAPGKGLEWVS**AISGSGGSTYYADS
VKGRFTISRDNSKNTLYLQMNSLRAEDTAVYYCASQHVGEQSRYFDY**WGQGTLVTVSSGGGG
GSDIVMTQSPSSLSASIGDRVTITCRASHSISSYVNWYQKKPGKAPNLLIYAASYLPRGVPSRFSG
SGLGTDFTLTISNLQPEDFATYYCQESYSTPYSFGQGTKVDIKRAAAEQKLISEEDLNGAAHHHH
HHC

SEQ ID NO:19
E9 cys-diabody sequence
QVQLQESGGGVVQPGRSLRLSCAASGFTFSSYGMHWVRQAPGKGLEWVS**AIGSSGGSTHDAD
TVKGRFTISRDNAKNSLYLQMNSLRAEDTAVYYCARDRARGFDY**WGQGTLVTVSSGGGGGSE
IVLTQSPSTLSASIGDRVTITCRASQGISSYLAWYQQKPGKAPKLLIYGASSLQSGVPSRFSGRGS
GADFTLTISSLQPEDFATYYCQQLISYPLTFGGGTKVEIKRAAAEQKLISEEDLNGAAHHHHHHC

SEQ ID NO:20
F1 cys-diabody sequence
QVQLVQSGAEVKKPGASVKVSCKASGYTFTDYYMHWVRQAPGEGLEWMG**WMNPNSGGTN
YAQKFQGRVTMTRDTSISTAYMELSRLRSDDTAVYYCARSHYWDS**WSPGTLVTVSSGGGGGS
SALTQPASVSGSPGQSITISCTGTSGDVGGYNYVSWYQQHPGKAPKLMIYDVSNRPSGVSNRFS
GSKSGNTASLTISGLQAEDEADYYCTSYAGSRNLVFGGGTKLTVLGAAAEQKLISEEDLNGAAH
HHHHC

SEQ ID NO:21
F11 cys-diabody sequence
QVQLQESGGGLLQPGGSLRLSCAASRFTFSNYAMSWVRQAPGKGLEWVS**AISGSGASTYYADS
VKGRFTISRDNSKNTLYLQMNSLRAEDTAVYYCSNLYGDYDY**WGQGTLVTVSSGGGGGSQSV
LTQPASVSGSPGQSITISCTGTSSDVGGYNYVSWYQQHPGKAPKLMIYDVSNRPSGVSNRFSGS
KSGNTASLTISGLQAEDEADYYCSSYTSSSTLLFGGGTKLTVLGAAAEQKLISEEDLNGAAHHH
HHC

SEQ ID NO:22
G1 cys-diabody sequence
QVQLQESGGGVVQPGGSLRLSCAASGFTFSSYSMNWVRQAPGKGLEWVS**SISSSSSYIYYADSV
KGRFTISRDNAKNSLYLQMNSLRAEDTAVYYCARDLPSDDYGDYDYYYGMDV**WGQGTTVT
VSSGGGGGSQSVLTQPPSASGTPGQRVTLFCSGSSSNIASNSVKWYQQPPQRAPKLLMF**SDDQR
PSGVPVRFSASKSGTSASLAISGLQSEDEADYYCAAWDDSLNAEV**FGGGTKVTVLGAAAEQKLI
SEEDLNGAAHHHHHHC

Figure 3 (Cont.)

SEQ ID NO:23
H2 cys-diabody sequence
EVQLVESGGGLVQPGGSLRLSCAASGFTFSTYAMSWVRQAPGKGLEWVS**AISGSGGSTYYADS
VKGRFTISRDNSKNTLYLQMNSLRAEDTAVYYCAREGGKWYYGMD**VWGRGTLVTVSSGGGG
GSSSELTQDPAVSVALGQTVRITCQGDSLRSYYTNWFQQKPGQAPLLVVYAKNKRPSGIPDRFS
GSGSGDTASLTITGAQAEDEADYYCNSRDSSGNYLFAAGTKLTVLGAAAEQKLISEEDLNGAAH
HHHHHC SEQ ID NO:24
H5 cys-diabody sequence
QVQLQESGGGLVQPGGSLRLSCAASGFTFSNYAMSWVRQAPGKGLEWVS**AISGSGGSTYYAD
SVKGRFTISRDNSKNTLYLQMNSLRAEDTAVYYCAKDRFRAAAY**WGQGTLVTVSSGGGGGSQ
SVLTQPPSVSAAPGQKVTISCTGSSSNIGAGYDVHWYQQLPGTAPKLLIYGNSNRPSGVPDRFSG
SKSGTSASLAISGLQSEDEADYYCAAWDDILNGEIFGGGTKVTVLGAAAEQKLISEEDLNGAAH
HHHHHC

Figure 4

SEQ ID NO:25
A12 ScFv sequence
QVQLVQSGGGLVQPGGSLRLSCAASGFTFSSYAMSWVRQAPGKGLEWVSAISGSGGSTYYAD SVKGRFTISRDNSKNTLYLQMNSLRAEDTAVYYCAKSSSSWYRSYYFDYWGQGTLVTVSSGGG GGSGGGGSGGGGSQSALTQDPAVSVALGQTVRITCRGDSLRNYYASWYQQKPGQAPVLVIYG KNNRPSGIPDRFSGSFSGNTASLTITGAQAEDEADYYCNSRDSSANQMFGGGTKVTVLG

SEQ ID NO:26
C2 ScFv sequence
QVQLQESGGGLVQPGGSLRLSCAASGFTFSSYAMSWVRQAPGKGLEWVSAISGSGGSTYYADS VKGRFTISRDNSKNTLYLQMNSLRAEDTAVYYCASQHVGEQSRYFDYWGQGTLVTVSSGGGG GSGGGGSGGGGSDIVMTQSPSSLSASIGDRVTITCRASHSISSYVNWYQKKPGKAPNLLIYAASY LPRGVPSRFSGSGLGTDFTLTISNLQPEDFATYYCQESYSTPYSFGQGTKVDIKR

SEQ ID NO:27
E9 ScFv sequence
QVQLQESGGGVVQPGRSLRLSCAASGFTFSSYGMHWVRQAPGKGLEWVSAIGSSGGSTHDAD TVKGRFTISRDNAKNSLYLQMNSLRAEDTAVYYCARDRARGFDYWGQGTLVTVSSGGGGGSG GGGSGGGGSEIVLTQSPSTLSASIGDRVTITCRASQGISSYLAWYQQKPGKAPKLLIYGASSLQSG VPSRFSGRGSGADFTLTISSLQPEDFATYYCQQLISYPLTFGGGTKVEIKR

SEQ ID NO:28
F1 ScFv sequence
QVQLVQSGAEVKKPGASVKVSCKASGYTFTDYYMHWVRQAPGEGLEWMGWMNPNSGGTN YAQKFQGRVTMTRDTSISTAYMELSRLRSDDTAVYYCARSHYWDSWSPGTLVTVSSGGGGGS GGGGSGGGGSSALTQPASVSGSPGQSITISCTGTSGDVGGYNYVSWYQQHPGKAPKLMIYDVS NRPSGVSNRFSGSKSGNTASLTISGLQAEDEADYYCTSYAGSRNLVFGGGTKLTVLG

SEQ ID NO:29
F11 ScFv sequence
QVQLQESGGGLLQPGGSLRLSCAASRFTFSNYAMSWVRQAPGKGLEWVSAISGSGASTYYADS VKGRFTISRDNSKNTLYLQMNSLRAEDTAVYYCSNLYGDYDYWGQGTLVTVSSGGGGGSGGG GSGGGGSQSVLTQPASVSGSPGQSITISCTGTSSDVGGYNYVSWYQQHPGKAPKLMIYDVSNRP SGVSNRFSGSKSGNTASLTISGLQAEDEADYYCSSYTSSSTLLFGGGTKLTVLG

SEQ ID NO:30
G1 ScFv sequence
QVQLQESGGGVVQPGGSLRLSCAASGFTFSSYSMNWVRQAPGKGLEWVSSISSSSSYIYYADSV KGRFTISRDNAKNSLYLQMNSLRAEDTAVYYCARDLPSDDYGDYDYYYYGMDVWGQGTTVT VSSGGGGGSGGGGSGGGGSQSVLTQPPSASGTPGQRVTLFCSGSSSNIASNSVKWYQQPPQRAP KLLMFSDDQRPSGVPVRFSASKSGTSASLAISGLQSEDEADYYCAAWDDSLNAEVFGGGTKVT VLG

Figure 4 (Cont.)

SEQ ID NO:31
H2 ScFv sequence
EVQLVESGGGLVQPGGSLRLSCAASGFTFSTYAMSWVRQAPGKGLEWVS**AISGSGGSTYYADS
VKGRFTISRDNSKNTLYLQMNSLRAEDTAVYYCAREGGKWYYGMD**VWGRGTLVTVSSGGGG
GSGGGGSGGGGSSSELTQDPAVSVALGQTVRITCQGDSLRSYYTNWFQQKPGQAPLLVVY**AKN
KRPSGIPDRFSGSGSGDTASLTITGAQAEDEADYYCNSRDSSGNYL**FAAGTKLTVLG SEQ ID NO:32
H5 ScFv sequence
QVQLQESGGGLVQPGGSLRLSCAASGFTFSNYAMSWVRQAPGKGLEWVS**AISGSGGSTYYAD
SVKGRFTISRDNSKNTLYLQMNSLRAEDTAVYYCAKDRFRAAAY**WGQGTLVTVSSGGGGGSG
GGGSGGGGSQSVLTQPPSVSAAPGQKVTISCTGSSSNIGAGYDVHWYQQLPGTAPKLLIY**GNSN
RPSGVPDRFSGSKSGTSASLAISGLQSEDEADYYCAAWDDILNGEI**FGGGTKVTVLG

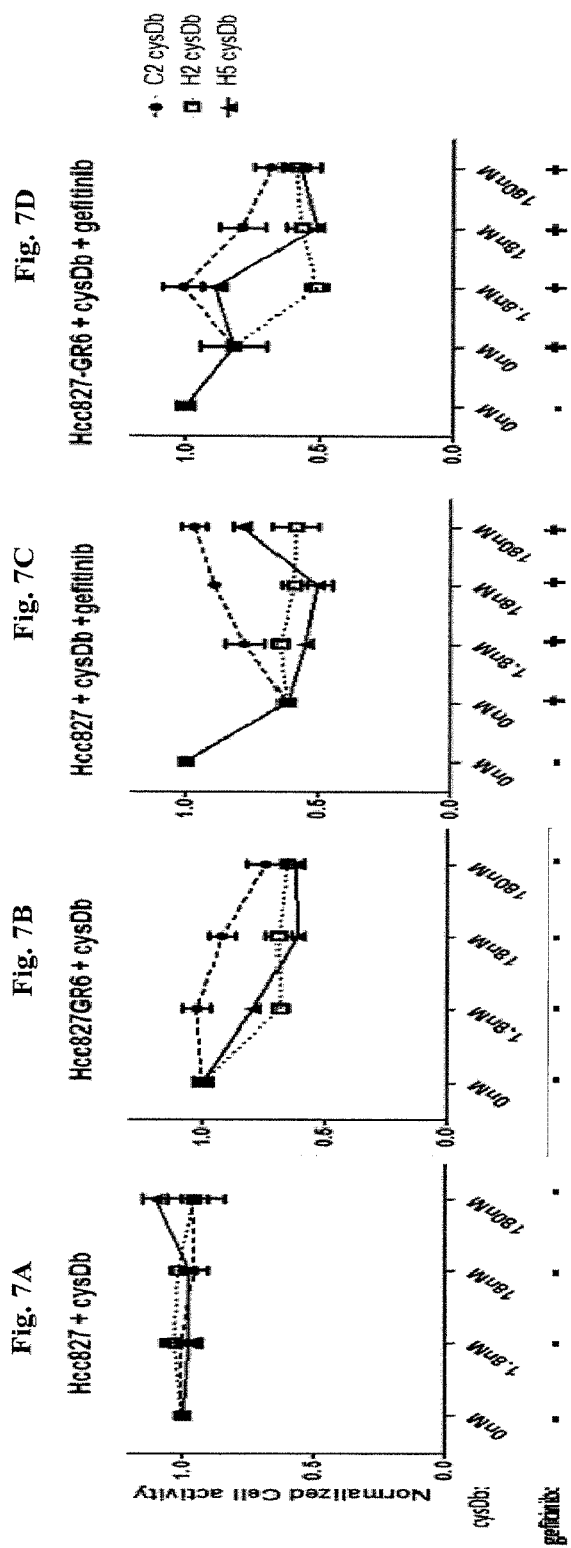

Oxidized
cys-diabody

Reduced
cys-diabody $K_d=2.0 \pm 0.3nM$ $K_d=0.60 \pm 0.07nM$ $K_d=4.7 \pm 0.8nM$

FULLY HUMAN ANTIBODIES AND FRAGMENTS RECOGNIZING HUMAN C-MET

CROSS REFERENCE TO RELATED APPLICATIONS

This application claims the benefit under 35 U.S.C. § 119(e) to U.S. Application No. 61/732,153 filed Nov. 30, 2012, the disclosure of which is incorporated by reference in its entirety.

STATEMENT AS TO RIGHTS TO INVENTIONS MADE UNDER FEDERALLY SPONSORED RESEARCH AND DEVELOPMENT

This invention was made with Government support of Grant No. NCI-U54 CA151459, awarded by the National Institutes of Health. The Government has certain rights in the invention.

FIELD OF THE INVENTION

This invention relates to anti-c-Met antibodies and antigen binding fragments thereof, their pharmaceutical compositions, and methods for using them in the detection and treatment of cancers that over express c-Met.

BACKGROUND OF THE INVENTION c-Met, a member of the tyrosine kinase superfamily, is the receptor for Hepatocyte Growth Factor (HGF). Binding of HGF to c-Met leads to receptor dimerization or multimerization, phosphorylation of multiple tyrosine residues in the intracellular region, catalytic activation, and downstream signaling. c-Met is also activated via ligand-independent mechanisms, including receptor over-expression, amplification, and mutation. c-Met activation enhances cellular proliferation, migration, morphogenesis, survival (including protection from apoptosis), and protease synthesis, characteristics that are associated with invasive cell phenotype and poor clinical outcomes and drug resistance in cancer patients. The c-Met signaling pathway is one of the most frequently dysregulated pathways in human cancers, and occurs in virtually all types of solid tumors.

c-Met is over-expressed in many different type of cancer cells and plays important role in mesenchymal-epithelial interaction and embryogenesis (X Liu et al, Trends in Molecular Medicine, 2009; E M Rosen et al, JCB, 1994; C Birchmeier et al, Trends in Cell Biology, 1998). It is also associated with drug resistance in lung cancer (J Engelman et al, Science, 2007). This makes it a useful target for therapeutic and diagnostic applications.

In addition to many small molecular inhibitors that have been studied for therapeutic effects, such as PHA-665752, SU11274, and ARQ197 (N Puri et al, Cancer Research, 2007; S Berthou et al, Oncogene, 2004; T Underiner et al, Anti-Cancer Agents in Medicinal Chemistry, 2010), there are also anti-MET antibodies that have been developed. Examples of anti-MET antibodies include the mouse monoclonal antibody DN-30 and the humanized one-armed monoclonal antibody onartuzumab. These antibodies have been evaluated for PET imaging applications (L R Perk et al, Eur J Nucl Med Mol Imaging, 2008; E M Jagoda et al, JNM, 2012).

There exists a need for antagonist antibodies to human c-Met, binding of which to the α-chain of human c-Met facilitates internalization of the receptor from the cell surface. There is also a need for antagonist antibodies to human c-Met, which binding to the α-chain of human c-Met facilitates internalization of the receptor from the cell surface in cells comprising c-Met variants containing gain of function mutations. There is also a need for antagonist antibodies to human c-Met which induce c-Met degradation and reduction of phosphorylated c-Met. Such antagonist activities could decrease the number of available binding sites for HGF on tumor cell surfaces, and terminate the pathway activation caused by overexpression, amplification, or mutation of c-Met. At the same time, such antagonist antibodies should inhibit HGF binding to c-Met and HGF-induced c-Met activation, and induce little or no agonist activity themselves.

The novel selection and characterization of several novel human scFv antibodies against human c-MET from a naive human scFv phage display library is described herein. scFv clones were confirmed to bind to cell surface target, and reformatted into cys-diabodies. Cys-diabodies have been successfully expressed in bacteria, cell lines, and tumor models and tested for affinity. The low immunogenicity, high affinity and varied pharmacokinetic characteristics of these fully human antibody fragments give them great potential in both in vivo and in vitro applications. Furthermore, the good affinity and low immunogenicity of these antibodies make them very useful for both in vivo and in vitro applications. These novel human antibodies can greatly help the study of drug resistance in EGFR targeted therapies, and improve the diagnosis and treatment of cancer patients.

BRIEF SUMMARY OF THE INVENTION

In one embodiment, an isolated human anti-c-Met antibody or antigen binding fragment thereof comprises a human heavy chain variable domain and a human light chain variable domain wherein the heavy chain variable domain comprises the amino acid sequence SEQ ID NOS:1, 2, 3, 4, 5, 6, 7, or 8, and the light chain variable domain comprises the amino acid sequence SEQ ID NOS:9, 10, 11, 12, 13, 14, 15, or 16.

In specific embodiments, the isolated human ant-c-Met antibody comprises the heavy chain variable domain amino acid sequence of SEQ ID NO:1 and the light chain variable domain amino acid sequence of SEQ ID NO:9. In specific embodiments, the isolated human ant-c-Met antibody comprises the heavy chain variable domain amino acid sequence of SEQ ID NO:2 and the light chain variable domain amino acid sequence of SEQ ID NO:10. In specific embodiments, the isolated human ant-c-Met antibody comprises the heavy chain variable domain amino acid sequence of SEQ ID NO:3 and the light chain variable domain amino acid sequence of SEQ ID NO:11. In specific embodiments, the isolated human ant-c-Met antibody comprises the heavy chain variable domain amino acid sequence of SEQ ID NO:4 and the light chain variable domain amino acid sequence of SEQ ID NO:12. In specific embodiments, the isolated human ant-c-Met antibody comprises the heavy chain variable domain amino acid sequence of SEQ ID NO:5 and the light chain variable domain amino acid sequence of SEQ ID NO:13. In specific embodiments, the isolated human ant-c-Met antibody comprises the heavy chain variable domain amino acid sequence of SEQ ID NO:6 and the light chain variable domain amino acid sequence of SEQ ID NO:14. In specific embodiments, the isolated human ant-c-Met antibody comprises the heavy chain variable domain amino acid sequence of SEQ ID NO:7 and the light chain variable domain amino acid sequence of SEQ ID NO:15. In specific embodiments, the isolated human ant-c-Met antibody comprises the heavy chain variable domain amino acid sequence of SEQ ID NO:8 and the light chain variable domain amino acid sequence of SEQ ID NO:16.

In one embodiment, the antibody or antigen binding fragment thereof is a diabody. In a specific embodiment the diabody is a cys-diabody. In a specific embodiment, the cys-diabody comprises the amino acid sequence SEQ ID NOS:17, 18, 19, 20, 21, 22, 23, or 24. In a specific embodiment the cys-diabody comprises the amino acid sequence SEQ ID NO:18. In a specific embodiment the cys-diabody comprises the amino acid sequence SEQ ID NO:19. In a specific embodiment the cys-diabody comprises the amino acid sequence SEQ ID NO:20. In a specific embodiment the cys-diabody comprises the amino acid sequence SEQ ID NO:21. In a specific embodiment the cys-diabody comprises the amino acid sequence SEQ ID NO:22. In a specific embodiment the cys-diabody comprises the amino acid sequence SEQ ID NO:23. In a specific embodiment the cys-diabody comprises the amino acid sequence SEQ ID NO:24.

In one embodiment, the isolated human anti-c-Met antibody or antigen binding fragment thereof is a single-chain variable fragment (ScFv). In a specific embodiment, the ScFv comprises the amino acid sequence SEQ ID NOS:25, 26, 27, 28, 29, 30, 31, or 32. In a specific embodiment the cys-diabody comprises the amino acid sequence SEQ ID NO:25. In a specific embodiment the ScFv comprises the amino acid sequence SEQ ID NOS:26. In a specific embodiment the cys-diabody comprises the amino acid sequence SEQ ID NO:27. In a specific embodiment the cys-diabody comprises the amino acid sequence SEQ ID NO:28. In a specific embodiment the cys-diabody comprises the amino acid sequence SEQ ID NO:29. In a specific embodiment the cys-diabody comprises the amino acid sequence SEQ ID NO:30. In a specific embodiment the ScFv comprises the amino acid sequence SEQ ID NOS:31. In a specific embodiment the ScFv comprises the amino acid sequence SEQ ID NOS:32.

In one embodiment the isolated human anti-c-Met antibody or antigen binding fragment thereof is a minibody or a triabody.

In one embodiment the isolated human anti-c-Met antibody or antigen binding fragment thereof is a fully human antibody.

In one embodiment the heavy chain variable region of the isolated human anti-c-Met antibody or antigen binding fragment thereof comprises three heavy chain complementary determining regions (HCDRs) and the light chain variable region of the isolated human anti-c-Met antibody or antigen binding fragment thereof comprises three light chain variable regions (LCDRs).

In one embodiment the isolated human anti-c-Met antibody or antigen binding fragment thereof of is monoclonal. In another embodiment the isolated human anti-c-Met antibody or antigen binding fragment thereof of is chimeric. In one embodiment the isolated human anti-c-Met antibody or antigen binding fragment thereof of is recombinant.

In one embodiment the isolated human anti-c-Met antibody or antigen binding fragment thereof of is conjugated to a cytotoxic agent. In a specific embodiment the cytotoxic agent is a chemotherapeutic agent. In a specific embodiment the chemotherapeutic agent is selected from the group consisting of gemcitabine, carboplatin, taxol, and paclitaxel.

In one embodiment the isolated human anti-c-Met antibody or antigen binding fragment thereof of is conjugated to a fluorescent molecule.

In one embodiment the isolated human anti-c-Met antibody or antigen binding fragment thereof of is radiolabeled. In a specific embodiment, the radiolabel is an iodine radiolabel.

In one embodiment the isolated human anti-c-Met antibody or antigen binding fragment thereof of has an affinity between 0.3 nM and 9.0 nM to c-Met.

In one embodiment, a pharmaceutical composition comprises the antibody isolated human anti-c-Met antibody or antigen binding fragment thereof of and a physiologically acceptable carrier. In a specific embodiment, the composition is administered by parenteral, subcutaneous, intraperitoneal, intrapulmonary, or intranasal administration. In a specific embodiment, the parenteral administration comprises intramuscular, intravenous, intraarterial, intraperitoneal, or subcutaneous administration. In one embodiment the pharmaceutical composition is co-administered with a cytotoxic agent.

In one embodiment, the invention relates to a method of diagnosis or prognosis for cancer in a subject wherein the increased expression of c-Met is detected by the antibody or antigen binding fragment thereof, wherein binding of the antibody or antigen binding fragment thereof is indicative of the presence of the cancer or the likelihood of the cancer progressing.

In one embodiment, the invention relates to a method for treating a patient for cancer, the method comprising administering to the patient an effective amount of the anti-c-Met antibody or antigen binding fragment thereof. In a specific embodiment, the method further comprises administering to the patient an effective amount of at least one additional anti-cancer agent. In a specific embodiment the at least one additional anti-cancer agent is selected from the group consisting of platinum-based chemotherapy drugs, taxanes, tyrosine kinase inhibitors, anti-EGFR antibodies, anti-ErbB2 antibodies, and combinations thereof.

In a specific embodiment the invention relates to the treatment, detection, or prognosis of lung cancer. In a specific embodiment the lung cancer is non-small cell lung cancer.

In one embodiment, the isolated human anti-c-Met cys-diabody comprises the amino acid sequence SEQ ID NOS: 17, 18, 19, 20, 21, 22, 23, or 24. In a specific embodiment, the isolated human anti-c-Met cys-diabody comprises the amino acid sequence SEQ ID NO:18. In a specific embodiment, the isolated human anti-c-Met cys-diabody comprises the amino acid sequence SEQ ID NO:23. In a specific embodiment, the isolated human anti-c-Met cys-diabody comprises the amino acid sequence SEQ ID NO:24.

In one embodiment, the anti-cMet antibody has a 6-histidine tag. In a specific embodiment the 6-histidine tag is enzymatically cleaved off after purification of the antibody.

In one embodiment the anti-cMet antibody has a Myc tag. In a specific embodiment the Myc tag is enzymatically cleaved off after purification of the antibody.

In one embodiment the anti-cMet antibody has a Myc tag and a 6-Histidine tag. In a specific embodiment the Myc tag and 6-Histidine tag is enzymatically cleaved off after purification of the antibody.

In one embodiment the anti-cMet antibody has a linker, a Myc tag, and a 6-histidine tag. In one embodiment the linker comprises the sequence AAAEQKLISEEDLNGAAHHHH-HHC. (SEQ ID NO:81)

In one embodiment the heavy chain variable domain sequence and light chain variable domain sequence of the anti-c-Met diabody of are linked by a sequences linker comprising the sequence GGGGGS. (SEQ ID NO:82)

In one embodiment the heavy chain variable domain sequence and light chain variable domain sequence of the anti-c-Met scFv antibody of are linked by a sequences linker comprising the sequence GGGGSGGGGSGGGGS. (SEQ ID NO:83)

In one embodiment the anti-cMet antibody has one or more terminal cysteines.

In one embodiment the one or more terminal cysteines is labeled with a detectable molecule. In specific embodiments the detectable molecule is a fluorophore, a radio label, a luminescent label, a chemoluminescent label, or a spin label.

In one embodiment, the anti-c-Met antibody or antigen binding fragment thereof is used in vaccine therapies for the cancer.

In one embodiment, the anti-c-Met antibody or antigen binding fragment thereof is used in in vivo diagnostics. In one embodiment, the anti-c-Met antibody or antigen binding fragment thereof is used in in vitro diagnostics.

In one embodiment, the anti-c-Met antibody or antigen binding fragment thereof is used in in vivo imaging. In one embodiment, the anti-c-Met antibody or antigen binding fragment thereof is used in in vitro imaging.

In one embodiment, the anti-c-Met antibody or antigen binding fragment thereof is used to detect abnormalities in mesenchymal-epithelial interactions. In one embodiment, the anti-c-Met antibody or antigen binding fragment thereof is used to diagnose diseases characterized by abnormalities in mesenchymal-epithelial interactions.

In one embodiment, the anti-c-Met antibody or antigen binding fragment thereof is used to detect abnormalities in embryogenesis. In one embodiment, the anti-c-Met antibody or antigen binding fragment thereof is used to diagnose diseases characterized by abnormalities in embryogenesis.

In one embodiment, the patient is human or mammal.

In one embodiment, the method further comprises a companion diagnostic.

BRIEF DESCRIPTION OF THE DRAWINGS

FIG. 1 depicts SEQ ID NOS:1-8. SEQ ID NOS:1-8 are the heavy chain variable domain sequences of the c-Met antibodies or antigen binding fragments thereof. Exemplary HCDRs and LCDRs of this invention are underlined.

FIG. 2 depicts SEQ ID NOS:9-16. SEQ ID NOS:9-16 are the light chain variable domain sequences of the c-Met antibodies or antigen binding fragments thereof. Exemplary HCDRs and LCDRs of this invention are underlined.

FIG. 3 depicts SEQ ID NOS:17-24. SEQ ID NOS:17-24 are the diabody sequences of the c-Met antibodies or antigen binding fragments thereof. Exemplary HCDRs and LCDRs of this invention are underlined.

FIG. 4 depicts SEQ ID NOS:24-32. SEQ ID NOS:25-32 are the scFv sequences of the c-Met antibodies or antigen binding fragments thereof. Exemplary HCDRs and LCDRs of this invention are underlined.

FIG. 7A-FIG. 7D depicts MTS assays show different effects of C2, H2 and H5 cys-diabodies on the growth of the sensitive Hcc827 cells and the resistant Hcc827-GR6 cells, with or without 1 µM of gefitinib.

FIG. 8A depicts the acquired drug resistance of cancer cells. FIG. 8B depicts the structure of a scFv, diabody, minibody, scFV-Fc, and intact antibody and their relative tumor uptakes and activity in blood compared to their injected dose. FIG. 8C depicts a nanoparticle containing an antibody, a magneto nano-sensor that can be used in in vitro detecting assays, and in vivo diagnostic imaging with an antibody. FIG. 8D depicts an oxidized and reduced cys-diabody.

DETAILED DESCRIPTION OF THE INVENTION

Overview

Figure 5A:
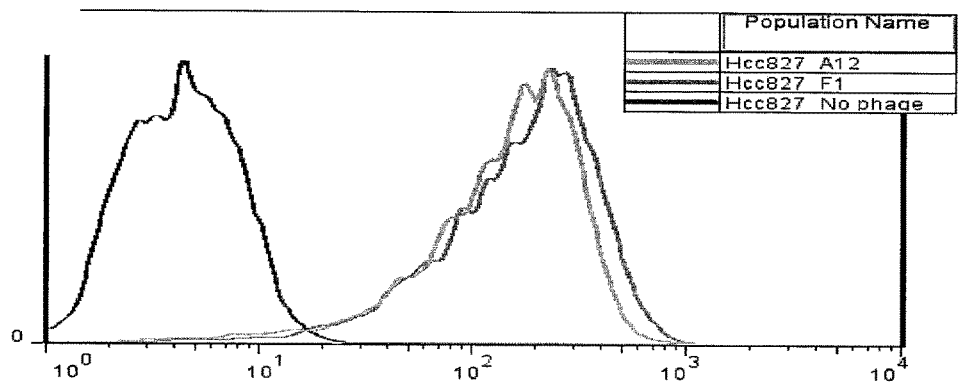
FIG. 5A-FIG. 5C depicts the phage flow cytometry experiments of A12, C2, E9, F1, F11, G1, H2, H5 show they can bind to cell surface MET.

EGFR targeted therapies, such as gefitinib or erlotinib treatment, have shown great potential in some non-small cell lung cancer patients. But such targeted therapies are only effective in small subsets of patients, and many patients that do respond to the treatment will eventually develop drug resistance. Better prediction and evaluation of drug resistance is needed for better treatment. Some biomarkers, such as MET, have been found to be correlated with the response to the targeted therapies (FIG. 8). Many different technologies can be employed to study and utilize these biomarkers to benefit cancer patients, such as antibody labeled nanoparticles and magneto nanosensors, and antibody based PET imaging (FIG. 8).

These technologies all require good antibodies in the right formats. Different antibody fragments have very different size, affinity and pharmacokinetics. While antibodies with Fc domains may be good for in vitro detection purposes, small fragments such as diabodies may be better for in vivo imaging because of shorter clearance times. FIG. 8 shows a summary of typical pharmacokinetic properties of 4 different antibody fragments and the intact antibody. We also engineered a special diabody called cys-diabody, which has a extra cysteine at the C-terminal of each polypeptide chain. These cysteines usually form a disulfide bond in the dimer, but are easily reduced after mild reduction for site specific labeling (FIG. 8).

Furthermore, while EGFR targeted therapies show great potential in some non-small cell lung cancer patients, their limited response rate calls for better prediction and evaluation of drug resistance. Antibodies against important biomarkers such as MET are very valuable for drug resistance evaluation and therapeutic applications. We successfully identified several novel human antibodies against MET from human scFv phage display libraries. The selected scFv clones were then re-formatted in to cys-diabodies or scFv-Fcs and expressed in bacteria or CHO cells. By flow cytometry using Hcc827 cells, we confirmed these antibody fragments have high affinities, ranging from 0.6 nM to 9 nM. These antibodies were then characterized and studied for therapeutic and diagnostic applications. Certain of the anti-MET cys-diabodies show therapeutic effects on erlotinib resistant cell lines with MET amplification. In conclusion, these novel human antibodies with high affinity and low immunogenicity can greatly help the study of drug resistance in EGFR targeted therapies, and improve the diagnosis and treatment of cancer patients.

Herein, the selection and characterization of several novel human scFv antibodies against human c-MET from a naive human scFv phage display library is described. scFv clones were confirmed to bind to cell surface target, and reformatted into cys-diabodies. Cys-diabodies have been successfully expressed in bacteria and tested for affinity. The low immunogenicity, high affinity and varied pharmacokinetic characteristics of these fully human antibody fragments give them great potential in both in vivo and in vitro applications.

Definitions

The term "inhibit" means the ability to substantially antagonize, prohibit, prevent, restrain, slow, disrupt, eliminate, stop, reduce, or reverse the biological effects of c-Met.

The term "treating" (or "treat" or "treatment") means slowing, interrupting, arresting, controlling, stopping, reducing, or reversing the progression or severity of a symptom, disorder, condition, or disease, but does not necessarily involve a total elimination of all disease-related symptoms, conditions, or disorders. The terms "treating," "treatment," and "therapy" as used herein refer to curative therapy, prophylactic therapy, and preventative therapy.

The term "effective amount" refers to the amount or dose of an antibody compound of the present invention which, upon single or multiple dose administration to a patient, provides the desired treatment or prevention. Therapeutically effective amounts of the present antibody compounds can comprise an amount in the range of from about 0.1 mg/kg to about 100 mg/kg per single dose. A therapeutically effective amount for any individual patient can be determined by the health care provider by monitoring the effect of the antibody compounds on a biomarker, such as cell surface c-Met in tumor or non-tumor tissues, tumor regression, etc. Analysis of the data obtained by these methods permits modification of the treatment regimen during therapy so that optimal amounts of antibody compounds, whether employed alone or in combination with one another therapeutic agent, are administered, and so that the duration of treatment can be determined as well. In this way, the dosing/treatment regimen can be modified over the course of therapy so that the lowest amounts of antibody compounds used alone or in combination that exhibit satisfactory tumor reducing effectiveness are administered, and so that administration of such compounds is continued only so long as is necessary to successfully treat the patient.

The antibody compounds of the present invention can be used as medicaments in human medicine, administered by a variety of routes. Most preferably, such compositions are for parenteral administration. Such pharmaceutical compositions can be prepared by methods well known in the art. See, e.g., Remington: The Science and Practice of Pharmacy, 19.sup.th ed. (1995), A. Gennaro et al., Mack Publishing Co., and comprise one or more antibody compounds disclosed herein, and a pharmaceutically acceptable carrier, diluent, or excipient.

The term "tumor" refers to all neoplastic cell growth and proliferation, whether malignant or benign, and all pre-cancerous and cancerous cells and tissues. The terms "cancer", "cancerous", and "tumor" are not mutually exclusive as used herein.

The terms "cancer" and "cancerous" refer to or describe the physiological condition in mammals that is typically characterized by aberrant cell growth/proliferation. Examples of cancers include, but are not limited to, carcinomas, lymphomas, blastomas, sarcomas, and leukemias. The terms "cancer" and "cancerous" further refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. "Mammal" for purposes of treatment refers to any animal classified as a mammal, including humans, domestic and farm animals, nonhuman primates, and zoo, sports, or pet animals, such as dogs, horses, cats, cows, etc The term "conjugate" is used herein according to its broadest definition to mean joined or linked together. Molecules are "conjugated" when they act or operate as if joined.

The term "antibody" is used in the broadest sense and specifically covers single anti-c-Met monoclonal antibodies (including agonist, antagonist, and neutralizing or blocking antibodies) and anti-c-Met antibody compositions with polyepitopic specificity. "Antibody" as used herein includes intact immunoglobulin or antibody molecules, polyclonal antibodies, multispecific antibodies (i.e., bispecific antibodies formed from at least two intact antibodies), antigen binding fragments of an antibody, and immunoglobulin fragments (such as Fab, F(ab').sub.2, or Fv), so long as they exhibit any of the desired agonistic or antagonistic properties described herein. The term "antibody" can also mean any "antibody fragments" and "antigen binding fragments thereof" wherein an antibody fragment or antigen binding fragment thereof comprise a portion of an intact antibody, generally the antigen binding or variable region of the intact antibody. Examples of antibody fragments include Fab, Fab', F(ab')2, and Fv fragments, diabodies, single chain antibody molecules, and multispecific antibodies formed from antibody fragments.

Antibodies are typically proteins or polypeptides which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V.sub.H) followed by a number of constant domains. Each light chain has a variable domain at one end (V.sub.L) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., J. Mol. Biol., 186:651-663 (1985); Novotny and Haber, Proc. Natl. Acad. Sci. USA, 82:4592-4596 (1985)). The light chains of antibodies from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

The term "variable" is used herein to describe certain portions of the variable domains, which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a .beta.-sheet configuration, connected by three CDRs, which form loops connecting, and in some cases forming part of, the .beta.-sheet structure. The CDRs in each chain are held together in close proximity by the FR regions and, with the CDRs from the other chain, contribute to the formation of the antigen binding site of antibodies [see Kabat, E. A. et al., Sequences of Proteins of Immunological Interest, National Institutes of Health, Bethesda, Md. (1987)]. The constant domains are not involved directly in binding an antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen.

The monoclonal antibodies herein include chimeric, hybrid and recombinant antibodies produced by splicing a variable (including hypervariable) domain of an anti-c-Met antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab').sub.2, and Fv), so long as they exhibit the desired biological activity or properties. See, e.g. U.S. Pat. No. 4,816,567 and Mage et al., in Monoclonal Antibody Production Techniques and Applications, pp. 79-97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature, 256:495 (1975), or may be made by recombinant DNA methods such as described in U.S. Pat. No. 4,816,567. The "monoclonal antibodies" may also be isolated from phage libraries generated using the techniques described in McCafferty et al., Nature, 348:552-554 (1990), for example.

A "diabody" refers to an engineered antibody construct prepared by isolating the binding domains (both heavy and light chain) of a binding antibody, and supplying a linking moiety which joins or operably links the heavy and light chains on the same polypeptide chain thereby preserving the binding function as described in detail by Holliger et al. (1993) Proc. Natl. Acad. Sci. USA 90:6444 and reviewed by Poljak (1994) Structure 2:1121-1123. This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. It should be clear that any method to generate diabodies, as for example described by Holliger, et al. (1993) supra, Poljak (1994) supra, Zhu, et al. (1996) Biotechnology 14:192-196, and U.S. Pat. No. 6,492,123, herein incorporated by reference, can be used. Once generated, the binding specificity can be determined by, for example, equilibrium methods (e.g., enzyme-linked immunoabsorbent assay (ELISA) or radioimmunoassay (RIA)), or kinetics (e.g. BIACORE™ analysis). Alternatively, the diabody can be subjected to other biological activity assays, e.g., bacterial aggregation or colognization assays, in order to evaluate its potency or pharmacological activity and potential efficacy as a therapeutic agent. Such assays are disclosed herein and are well-known in the art.

A "human antibody" is one which possesses an amino acid sequence which corresponds to that of an antibody produced by a human and/or has been made using any of the techniques for making human antibodies known in the art or as disclosed herein. This definition of a human antibody includes antibodies comprising at least one human heavy chain polypeptide or at least one human light chain polypeptide, for example an antibody comprising murine light chain and human heavy chain polypeptides. Human antibodies can be produced using various techniques known in the art. In one embodiment, the human antibody is selected from a phage library, where that phage library expresses human antibodies (Vaughan et al. Nature Biotechnology, 14:309-314 (1996): Sheets et al. PNAS, (USA) 95:6157-6162 (1998)); Hoogenboom and Winter, J. Mol. Biol., 227:381 (1991); Marks et al., J. Mol. Biol., 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology, 10: 779-783 (1992); Lonberg et al., Nature, 368: 856-859 (1994); Morrison, Nature, 368:812-13 (1994); Fishwild et al., Nature Biotechnology, 14: 845-51 (1996); Neuberger, Nature Biotechnology, 14: 826 (1996); Lonberg and Huszar, Intern. Rev. Immunol., 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., J. Immunol., 147 (1):86-95 (1991); and U.S. Pat. No. 5,750,373.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Ye^{90}$, $Re^{186}$, $Re^{188}$, $Sm^{153}$, $Bi^{212}$, $P^{32}$ radioactive isotopes of Lu, and any other radioactive isotope known to one skilled in the art), chemotherapeutic agents, and toxins such as small molecule toxins or enzymatically active toxins of bacterial, fungal, plant or animal origin, including fragments and/or variants thereof. Cytotoxic agents also include recomvinant immunotoxins (e.g. LMB7, LMB9, LMB2, BL22, SS1, MR1, TGFα-PE38, IL3/13-PE38, DT-IL2, DT-GM-CSF). Cytotoxic agents also include toxins (e.g. ricin, botulinum, Coley toxins). Cytotoxic agents also include anti-angiogenesis agents, anti-mitotic agents, nucleoside antagonists, intercalating agents, spindle inhibitors, folate inhibitors, alkylating agents, anti-metabolites, anti-tumor antibiotics, topoisomerase inhibitors, corticosteroids, and differentiating agents.

A "chemotherapeutic agent" is a chemical compound useful in the treatment of conditions like cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (.sub.1.sup.I and calicheamicin 2.sup.I.sub.1, see, e.g., Agnew Chem Intl. Ed. Engl. 33:183-186 (1994); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rh{circle around (o)}ne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "mammal" as used herein refers to any mammal classified as a mammal, including humans, higher primates, cows, horses, dogs and cats. In a preferred embodiment of the invention, the mammal is a human.

Antibodies

The antibodies of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the c-Met polypeptide (or a c-Met ECD) or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for c-Met antibody titer. If desired, the mammal can be boosted until the antibody titer increases or plateaus.

The antibodies of the invention may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The antibodies of the invention may, alternatively, be humanized antibodies. Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody.

Accordingly, such "humanized" antibodies are chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

The antibodies of the invention may, alternatively, be human monoclonal antibodies. Human monoclonal antibodies can be made by the hybridoma method. Human myeloma and mouse-human heteromyeloma cell lines for the production of human monoclonal antibodies have been described, for example, by Kozbor, J. Immunol. 133, 3001 (1984), and Brodeur, et al., Monoclonal Antibody Production Techniques and Applications, pp. 51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region (J.sub.H) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., Proc. Natl. Acad. Sci. USA 90, 2551-255 (1993); Jakobovits et al., Nature 362, 255-258 (1993).

Mendez et al. (Nature Genetics 15: 146-156 [1997]) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous J.sub.H segment as described above. The Xenomouse II harbors 1,020 kb of human heavy chain locus containing approximately 66 V.sub.H genes, complete D.sub.H and J.sub.H regions and three different constant regions (.mu., .delta. and .chi.), and also harbors 800 kb of human .kappa. locus containing 32 V.kappa. genes, J.kappa. segments and C.kappa. genes. The antibodies produced in these mice closely resemble that seen in humans in all respects, including gene rearrangement, assembly, and repertoire. The human antibodies are preferentially expressed over endogenous antibodies due to deletion in endogenous J.sub.H segment that prevents gene rearrangement in the murine locus.

Alternatively, the phage display technology (McCafferty et al., Nature 348, 552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S. and Chiswell, David J., Current Opinion in Structural Biology 3, 564-571 (1993). Several sources of V-gene segments can be used for phage display. Clackson et al., Nature 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222, 581-597 (1991), or Griffith et al., EMBO J. 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol. 10, 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al., Nucl. Acids Res. 21, 2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published 1 Apr. 1993). Unlike traditional humanization of rodent antibodies by CDR grafting, this technique provides completely human antibodies, which have no framework or CDR residues of rodent origin.

As discussed in detail below, the antibodies of the invention may optionally comprise monomeric, antibodies, dimeric antibodies, as well as multivalent forms of antibodies. Those skilled in the art may construct such dimers or multivalent forms by techniques known in the art and using the c-Met antibodies herein. Methods for preparing monovalent antibodies are also well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

The antibodies of this invention may be diabody derivatives. The diabody derivatives of the present invention are advantageously useful over other antibody and antibody fragments known in the art because they are easy to express in large quantities, can penetrate tissues easily and lack the constant domains that promote often unwanted and usually superfluous effector functions. Further, because the diabodies of the invention are not of murine origin, they do not provoke an immune reaction in the human host, leading to rapid clearance and poor efficacy during long-term treatment. Since dental caries tend to be chronic rather than acute, murine antibodies are of little benefit to patients in the long-term. While scFvs to SAI/II have been produced (Ma, et al. (1990) supra), there are two drawbacks of scFvs compared to the ideal sIgA format, monovalency and instability. ScFvs are monovalent because the heavy and light chains are joined by a flexible peptide linker, which allows the two domains to fold and interact with each other. By using diabodies, wherein the linking peptide is shortened thereby forcing the heavy and light chain variable domains to interact to form a dimer, the drawback of using scFvs is overcome. Further, as a consequence of this interaction, the diabody is bivalent like the parent immunoglobulin, and therefore has increased binding avidity.

Heteroconjugate antibodies are also within the scope of the present invention. Heteroconjugate antibodies are composed of two covalently joined antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

In certain embodiments, the anti-c-Met antibody is an antibody fragment. Various techniques have been developed for the production of antibody fragments. Traditionally, these fragments were derived via proteolytic digestion of intact antibodies (see, e.g., Morimoto et al., J. Biochem. Biophys. Methods 24:107-117 (1992) and Brennan et al., Science 229:81 (1985)). However, these fragments can now be produced directly by recombinant host cells. For example, Fab'-SH fragments can be directly recovered from *E. coli* and chemically coupled to form F(ab').sub.2 fragments (Carter et al., Bio/Technology 10:163-167 (1992)). In another embodiment, the F(ab').sub.2 is formed using the leucine zipper GCN4 to promote assembly of the F(ab').sub.2 molecule. According to another approach, Fv, Fab or F(ab').sub.2 fragments can be isolated directly from recombinant host cell culture. A variety of techniques for the production of antibody fragments will be apparent to the skilled practitioner. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an F(ab').sub.2 fragment that has two antigen combining sites and is still capable of cross-linking antigen.

The Fab fragments produced in the antibody digestion also contain the constant domains of the light chain and the first constant domain (CHi) of the heavy chain. Fab' fragments differ from Fab fragments by the addition of a few residues at the carboxy terminus of the heavy chain CHi domain including one or more cysteines from the antibody hinge region. Fab'-SH is the designation herein for Fab' in which the cysteine residue(s) of the constant domains bear a free thiol group. F(ab').sub.2 antibody fragments originally were produced as pairs of Fab' fragments which have hinge cysteines between them. Other chemical couplings of antibody fragments are also known.

In certain embodiments, there are amino acid sequence variants of the anti-c-Met antibody. These variants are prepared by introducing appropriate nucleotide changes into the anti-c-Met antibody DNA, or by peptide synthesis. Such variants include, for example, deletions from, and/or insertions into and/or substitutions of, residues within the amino acid sequences of the anti-c-Met antibodies of the examples herein. Any combination of deletion, insertion, and substitution is made to arrive at the final construct, provided that the final construct possesses the desired characteristics. The amino acid changes also may alter post-translational processes of the humanized or variant anti-c-Met antibody, such as changing the number or position of glycosylation sites.

A useful method for identification of certain residues or regions of the anti-c-Met antibody that are preferred locations for mutagenesis is called "alanine scanning mutagenesis," as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with c-Met antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-c-Met antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-c-Met antibody with an N-terminal methionyl residue or the antibody fused to an epitope tag. Other insertional variants of the anti-c-Met antibody molecule include the fusion to the N- or C-terminus of the anti-c-Met antibody of an enzyme or a polypeptide or polyol which increases the serum half-life of the antibody.

The antibodies of this invention can be conjugated to secondary molecules. The antibodies can be conjugated to fluorophores, radioactive isotopes, chemoluminescent molecules, chemotherapeutic molecules, cytotoxic molecules, anti-viral molecules, antibiotic molecules, and any other imaging or diagnostic molecule known to one of skill in the art.

In specific embodiments of this invention, the isolated human ant-c-Met antibody comprises the heavy chain variable domain amino acid sequence of SEQ ID NO:1 and the light chain variable domain amino acid sequence of SEQ ID NO:9 (i.e., the "A12 antibody"):

```
                                              SEQ ID NO: 1
QVQLVQSGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSS

SSWYRSYYFDYWGQGTLVTVSS

SEQ ID NO: 9
QSALTQDPAVSVALGQTVRITCRGDSLRNYYASWYQQKPGQAPVLVIYGK

NNRPSGIPDRFSGSFSGNTASLTITGAQAEDEADYYCNSRDSSANQMFGG

GTKVTVLG
```

In specific embodiments, the isolated human ant-c-Met antibody comprises the heavy chain variable domain amino acid sequence of SEQ ID NO:2 and the light chain variable domain amino acid sequence of SEQ ID NO:10 (i.e., the "C2 antibody"):

```
                                              SEQ ID NO: 2
QVQLQESGGGLVQPGGSLRLSCAASGFTFSSYAMSWVRQAPGKGLEWVSA

ISGSGGSTYYADSVKGRFTISRDNSKNTLYLQMNSLRAEDTAVYYCASQH

VGEQSRYFDYWGQGTLVTVSS

SEQ ID NO: 10
DIVMTQSPSSLSASIGDRVTITCRASHSISSYVNWYQKKPGKAPNLLIYA

ASYLPRGVPSRFSGSGLGTDFTLTISNLQPEDFATYYCQESYSTPYSFGQ

GTKVDIKR
```

In specific embodiments, the isolated human ant-c-Met antibody comprises the heavy chain variable domain amino acid sequence of SEQ ID NO:3 and the light chain variable domain amino acid sequence of SEQ ID NO:11 (i.e., the "E9 antibody").

```
                                              SEQ ID NO: 3
QVQLQESGGGVVQPGRSLRLSCAASGFTFSSYGMHWVRQAPGKGLEWVSA

IGSSGGSTHDADTVKGRFTISRDNAKNSLYLQMNSLRAEDTAVYYCARDR

ARGFDYWGQGTLVTVSS

SEQ ID NO: 11
EIVLTQSPSTLSASIGDRVTITCRASQGISSYLAWYQQKPGKAPKLLIYG

ASSLQSGVPSRFSGRGSGADFTLTISSLQPEDFATYYCQQLISYPLTFGG

GTKVEIKR
```

In specific embodiments, the isolated human ant-c-Met antibody comprises the heavy chain variable domain amino acid sequence of SEQ ID NO:4 and the light chain variable domain amino acid sequence of SEQ ID NO:12 (i.e., the "F1 antibody").

```
                                              SEQ ID NO: 4
QVQLVQSGAEVKKPGASVKVSCKASGYTFTDYYMHWVRQAPGEGLEWMGW

MNPNSGGTNYAQKFQGRVTMTRDTSISTAYMELSRLRSDDTAVYYCARSH

YWDSWSPGTLVTVSS

SEQ ID NO: 12
SALTQPASVSGSPGQSITISCTGTSGDVGGYNYVSWYQQHPGKAPKLMIY

DVSNRPSGVSNRFSGSKSGNTASLTISGLQAEDEADYYCTSYAGSRNLVF

GGGTKLTVLG
```

In specific embodiments, the isolated human ant-c-Met antibody comprises the heavy chain variable domain amino acid sequence of SEQ ID NO:5 and the light chain variable domain amino acid sequence of SEQ ID NO:13 (i.e., the "F11 antibody").

```
                                              SEQ ID NO: 5
QVQLQESGGGLLQPGGSLRLSCAASRFTFSNYAMSWVRQAPGKGLEWVSA

ISGSGASTYYADSVKGRFTISRDNSKNTLYLQMNSLRAEDTAVYYCSNLY

GDYDYWGQGTLVTVSS

SEQ ID NO: 13
QSVLTQPASVSGSPGQSITISCTGTSSDVGGYNYVSWYQQHPGKAPKLMI

YDVSNRPSGVSNRFSGSKSGNTASLTISGLQAEDEADYYCSSYTSSSTLL

FGGGTKLTVLG
```

In specific embodiments, the isolated human ant-c-Met antibody comprises the heavy chain variable domain amino acid sequence of SEQ ID NO:6 and the light chain variable domain amino acid sequence of SEQ ID NO:14 (i.e., the "G1 antibody").

```
                                              SEQ ID NO: 6
QVQLQESGGGVVQPGGSLRLSCAASGFTFSSYSMNWVRQAPGKGLEWVSS

ISSSSSYIYYADSVKGRFTISRDNAKNSLYLQMNSLRAEDTAVYYCARDL

PSDDYGDYDYYYYGMDVWGQGTTVTVSS
```

```
                                                    SEQ ID NO: 14
QSVLTQPPSASGTPGQRVTLFCSGSSSNIASNSVKWYQQPPQRAPKLLMF

SDDQRPSGVPVRFSASKSGTSASLAISGLQSEDEADYYCAAWDDSLNAEV

FGGGTKVTVLG
```

In specific embodiments, the isolated human ant-c-Met antibody comprises the heavy chain variable domain amino acid sequence of SEQ ID NO:7 and the light chain variable domain amino acid sequence of SEQ ID NO:15 (i.e., the "H2 antibody").

```
                                                     SEQ ID NO: 7
EVQLVESGGGLVQPGGSLRLSCAASGFTFSTYAMSWVRQAPGKGLEWVSA

ISGSGGSTYYADSVKGRFTISRDNSKNTLYLQMNSLRAEDTAVYYCAREG

GKWYYGMDVWGRGTLVTVSS
                                                    SEQ ID NO: 15
SSELTQDPAVSVALGQTVRITCQGDSLRSYYTNWFQQKPGQAPLLVVYAK

NKRPSGIPDRFSGSGSGDTASLTITGAQAEDEADYYCNSRDSSGNYLFAA

GTKLTVLG
```

In specific embodiments, the isolated human ant-c-Met antibody comprises the heavy chain variable domain amino acid sequence of SEQ ID NO:8 and the light chain variable domain amino acid sequence of SEQ ID NO:16 (i.e., the "H5 antibody").

```
                                                     SEQ ID NO: 8
QVQLQESGGGLVQPGGSLRLSCAASGFTFSNYAMSWVRQAPGKGLEWVSA

ISGSGGSTYYADSVKGRFTISRDNSKNTLYLQMNSLRAEDTAVYYCAKDR

FRAAAYWGQGTLVTVSS
                                                    SEQ ID NO: 16
QSVLTQPPSVSAAPGQKVTISCTGSSSNIGAGYDVHWYQQLPGTAPKLLI

YGNSNRPSGVPDRFSGSKSGTSASLAISGLQSEDEADYYCAAWDDILNGE

IFGGGTKVTVLG
```

In specific embodiments of this invention, the isolated human ant-c-Met antibody is a cys-diabody which comprises SEQ ID NO:17, inclusive of the 6-His tag which can be removed using techniques known to one of skill in the art, for example by cleavage (i.e., the "A12 cys-diabody"):

```
                                                    SEQ ID NO: 17
QVQLVQSGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSS

SSWYRSYYFDYWGQGTLVTVSSGGGGGSQSALTQDPAVSVALGQTVRITC

RGDSLRNYYASWYQQKPGQAPVLVIYGKNNRPSGIPDRFSGSFSGNTASL

TITGAQAEDEADYYCNSRDSSANQMFGGGTKVTVLGAAAEQKLISEEDLN

GAAHHHHHHC
```

In specific embodiments of this invention, the isolated human ant-c-Met antibody is a cys-diabody which comprises SEQ ID NO:18, inclusive of the 6-His tag which can be removed using techniques known to one of skill in the art, for example by cleavage (i.e., the "C2 cys-diabody"):

```
                                                    SEQ ID NO: 18
QVQLQESGGGLVQPGGSLRLSCAASGFTFSSYAMSWVRQAPGKGLEWVSA

ISGSGGSTYYADSVKGRFTISRDNSKNTLYLQMNSLRAEDTAVYYCASQH

VGEQSRYFDYWGQGTLVTVSSGGGGGSDIVMTQSPSSLSASIGDRVTITC

RASHSISSYVNWYQKKPGKAPNLLIYAASYLPRGVPSRFSGSGLGTDFTL

TISNLQPEDFATYYCQESYSTPYSFGQGTKVDIKRAAAEQKLISEEDLNG

AAHHHHHHC
```

In specific embodiments of this invention, the isolated human ant-c-Met antibody is a cys-diabody which comprises SEQ ID NO:19, inclusive of the 6-His tag which can be removed using techniques known to one of skill in the art, for example by cleavage (i.e., the "E9 cys-diabody"):

```
                                                    SEQ ID NO: 19
QVQLQESGGGVVQPGRSLRLSCAASGFTFSSYGMHWVRQAPGKGLEWVSA

IGSSGGSTHDADTVKGRFTISRDNAKNSLYLQMNSLRAEDTAVYYCARDR

ARGFDYWGQGTLVTVSSGGGGGSEIVLTQSPSTLSASIGDRVTITCRASQ

GISSYLAWYQQKPGKAPKLLIYGASSLQSGVPSRFSGRGSGADFTLTISS

LQPEDFATYYCQQLISYPLTFGGGTKVEIKRAAAEQKLISEEDLNGAAHH

HHHHC
```

In specific embodiments of this invention, the isolated human ant-c-Met antibody is a cys-diabody which comprises SEQ ID NO:20, inclusive of the 6-His tag which can be removed using techniques known to one of skill in the art, for example by cleavage (i.e., the "F1 cys-diabody"):

```
                                                    SEQ ID NO: 20
QVQLVQSGAEVKKPGASVKVSCKASGYTFTDYYMHWVRQAPGEGLEWMGW

MNPNSGGTNYAQKFQGRVTMTRDTSISTAYMELSRLRSDDTAVYYCARSH

YWDSWSPGTLVTVSSGGGGGSSALTQPASVSGSPGQSITISCTGTSGDVG

GYNYVSWYQQHPGKAPKLMIYDVSNRPSGVSNRFSGSKSGNTASLTISGL

QAEDEADYYCTSYAGSRNLVFGGGTKLTVLGAAAEQKLISEEDLNGAAHH

HHHHC
```

In specific embodiments of this invention, the isolated human ant-c-Met antibody is a cys-diabody which comprises SEQ ID NO:21, inclusive of the 6-His tag which can be removed using techniques known to one of skill in the art, for example by cleavage (i.e., the "F11 cys-diabody"):

```
                                                    SEQ ID NO: 21
QVQLQESGGGLLQPGGSLRLSCAASRFTFSNYAMSWVRQAPGKGLEWVSA

ISGSGASTYYADSVKGRFTISRDNSKNTLYLQMNSLRAEDTAVYYCSNLY

GDYDYWGQGTLVTVSSGGGGGSQSVLTQPASVSGSPGQSITISCTGTSSD

VGGYNYVSWYQQHPGKAPKLMIYDVSNRPSGVSNRFSGSKSGNTASLTIS

GLQAEDEADYYCSSYTSSSTLLFGGGTKLTVLGAAAEQKLISEEDLNGAA

HHHHHHC
```

In specific embodiments of this invention, the isolated human ant-c-Met antibody is a cys-diabody which comprises SEQ ID NO:22, inclusive of the 6-His tag which can be removed using techniques known to one of skill in the art, for example by cleavage (i.e., the "G1 cys-diabody"):

SEQ ID NO: 22
QVQLQESGGGVVQPGGSLRLSCAASGFTFSSYSMNWVRQAPGKGLEWVSS

ISSSSSYIYYADSVKGRFTISRDNAKNSLYLQMNSLRAEDTAVYYCARDL

PSDDYGDYDYYYGMDVWGQGTTVTVSSGGGGGSQSVLTQPPSASGTPGQ

RVTLFCSGSSSNIASNSVKWYQQPPQRAPKLLMFSDDQRPSGVPVRFSAS

KSGTSASLAISGLQSEDEADYYCAAWDDSLNAEVFGGGTKVTVLGAAAEQ

KLISEEDLNGAAHHHHHHC

In specific embodiments of this invention, the isolated human ant-c-Met antibody is a cys-diabody which comprises SEQ ID NO:23, inclusive of the 6-His tag which can be removed using techniques known to one of skill in the art, for example by cleavage (i.e., the "H2 cys-diabody"):

SEQ ID NO: 23
EVQLVESGGGLVQPGGSLRLSCAASGFTFSTYAMSWVRQAPGKGLEWVSA

ISGSGGSTYYADSVKGRFTISRDNSKNTLYLQMNSLRAEDTAVYYCAREG

GKWYYGMDVWGRGTLVTVSSGGGGGSSSELTQDPAVSVALGQTVRITCQG

DSLRSYYTNWFQQKPGQAPLLVVYAKNKRPSGIPDRFSGSGSGDTASLTI

TGAQAEDEADYYCNSRDSSGNYLFAAGTKLTVLGAAAEQKLISEEDLNGA

AHHHHHHC

In specific embodiments of this invention, the isolated human ant-c-Met antibody is a cys-diabody which comprises SEQ ID NO:24, inclusive of the 6-His tag which can be removed using techniques known to one of skill in the art, for example by cleavage (i.e., the "H5 cys-diabody"):

SEQ ID NO: 24
QVQLQESGGGLVQPGGSLRLSCAASGFTFSNYAMSWVRQAPGKGLEWVSA

ISGSGGSTYYADSVKGRFTISRDNSKNTLYLQMNSLRAEDTAVYYCAKDR

FRAAAYWGQGTLVTVSSGGGGGSQSVLTQPPSVSAAPGQKVTISCTGSSS

NIGAGYDVHWYQQLPGTAPKLLIYGNSNRPSGVPDRFSGSKSGTSASLAI

SGLQSEDEADYYCAAWDDILNGEIFGGGTKVTVLGAAAEQKLISEEDLNG

AAHHHHHHC

In specific embodiments of this invention, the isolated human ant-c-Met antibody is a ScFv antibody which comprises SEQ ID NO:25 (i.e., the "A12 ScFv antibody"):

SEQ ID NO: 25
QVQLVQSGGGLVQPGGSLRLSCAASGFTFSSYAMSWVRQAPGKGLEWVSA

ISGSGGSTYYADSVKGRFTISRDNSKNTLYLQMNSLRAEDTAVYYCAKSS

SSWYRSYYFDYWGQGTLVTVSSGGGGGSGGGGSGGGGSQSALTQDPAVSV

ALGQTVRITCRGDSLRNYYASWYQQKPGQAPVLVIYGKNNRPSGIPDRFS

GSFSGNTASLTITGAQAEDEADYYCNSRDSSANQMFGGGTKVTVLG

In specific embodiments of this invention, the isolated human ant-c-Met antibody is a ScFv antibody which comprises SEQ ID NO:26 (i.e., the "C2 ScFv antibody"):

SEQ ID NO: 26
QVQLQESGGGLVQPGGSLRLSCAASGFTFSSYAMSWVRQAPGKGLEWVSA

ISGSGGSTYYADSVKGRFTISRDNSKNTLYLQMNSLRAEDTAVYYCASQH

VGEQSRYFDYWGQGTLVTVSSGGGGGSGGGGSGGGGSDIVMTQSPSSLSA

SIGDRVTITCRASHSISSYVNWYQKKPGKAPNLLIYAASYLPRGVPSRFS

GSGLGTDFTLTISNLQPEDFATYYCQESYSTPYSFGQGTKVDIKR

In specific embodiments of this invention, the isolated human ant-c-Met antibody is a ScFv antibody which comprises SEQ ID NO:27 (i.e., the "E9 ScFv antibody"):

SEQ ID NO: 27
QVQLQESGGGVVQPGRSLRLSCAASGFTFSSYGMHWVRQAPGKGLEWVSA

IGSSGGSTHDADTVKGRFTISRDNAKNSLYLQMNSLRAEDTAVYYCARDR

ARGFDYWGQGTLVTVSSGGGGGSGGGGSGGGGSEIVLTQSPSTLSASIGD

RVTITCRASQGISSYLAWYQQKPGKAPKLLIYGASSLQSGVPSRFSGRGS

GADFTLTISSLQPEDFATYYCQQLISYPLTFGGGTKVEIKR

In specific embodiments of this invention, the isolated human ant-c-Met antibody is a ScFv antibody which comprises SEQ ID NO:28 (i.e., the "F1 ScFv antibody"):

SEQ ID NO: 28
QVQLVQSGAEVKKPGASVKVSCKASGYTFTDYYMHWVRQAPGEGLEWMGW

MNPNSGGTNYAQKFQGRVTMTRDTSISTAYMELSRLRSDDTAVYYCARSH

YWDSWSPGTLVTVSSGGGGGSGGGGSGGGGSSALTQPASVSGSPGQSITI

SCTGTSGDVGGYNYVSWYQQHPGKAPKLMIYDVSNRPSGVSNRFSGSKSG

NTASLTISGLQAEDEADYYCTSYAGSRNLVFGGGTKLTVLG

In specific embodiments of this invention, the isolated human ant-c-Met antibody is a ScFv antibody which comprises SEQ ID NO:29 (i.e., the "F11 ScFv antibody"):

SEQ ID NO: 29
QVQLQESGGGLLQPGGSLRLSCAASRFTFSNYAMSWVRQAPGKGLEWVSA

ISGSGASTYYADSVKGRFTISRDNSKNTLYLQMNSLRAEDTAVYYCSNLY

GDYDYWGQGTLVTVSSGGGGGSGGGGSGGGGSQSVLTQPASVSGSPGQSI

TISCTGTSSDVGGYNYVSWYQQHPGKAPKLMIYDVSNRPSGVSNRFSGSK

SGNTASLTISGLQAEDEADYYCSSYTSSSTLLFGGGTKLTVLG

In specific embodiments of this invention, the isolated human ant-c-Met antibody is a ScFv antibody which comprises SEQ ID NO:30 (i.e., the "G1 ScFv antibody"):

SEQ ID NO: 30
QVQLQESGGGVVQPGGSLRLSCAASGFTFSSYSMNWVRQAPGKGLEWVSS

ISSSSSYIYYADSVKGRFTISRDNAKNSLYLQMNSLRAEDTAVYYCARDL

PSDDYGDYDYYYGMDVWGQGTTVTVSSGGGGGSGGGGSGGGGSQSVLTQ

PPSASGTPGQRVTLFCSGSSSNIASNSVKWYQQPPQRAPKLLMFSDDQRP

SGVPVRFSASKSGTSASLAISGLQSEDEADYYCAAWDDSLNAEVFGGGTK

VTVLG

In specific embodiments of this invention, the isolated human ant-c-Met antibody is a ScFv antibody which comprises SEQ ID NO:31 (i.e., the "H2 ScFv antibody"):

SEQ ID NO: 31
EVQLVESGGGLVQPGGSLRLSCAASGFTFSTYAMSWVRQAPGKGLEWVSA

ISGSGGSTYYADSVKGRFTISRDNSKNTLYLQMNSLRAEDTAVYYCAREG

GKWYYGMDVWGRGTLVTVSSGGGGSGGGGSGGGGSSSELTQDPAVSVAL

GQTVRITCQGDSLRSYYTNWFQQKPGQAPLLVVYAKNKRPSGIPDRFSGS

GSGDTASLTITGAQAEDEADYYCNSRDSSGNYLFAAGTKLTVLG

In specific embodiments of this invention, the isolated human ant-c-Met antibody is a ScFv antibody which comprises SEQ ID NO:32 (i.e., the "H5 ScFv antibody"):

SEQ ID NO: 32
QVQLQESGGGLVQPGGSLRLSCAASGFTFSNYAMSWVRQAPGKGLEWVSA

ISGSGGSTYYADSVKGRFTISRDNSKNTLYLQMNSLRAEDTAVYYCAKDR

FRAAAYWGQGTLVTVSSGGGGSGGGGSGGGGSQSVLTQPPSVSAAPGQK

VTISCTGSSSNIGAGYDVHWYQQLPGTAPKLLIYGNSNRPSGVPDRFSGS

KSGTSASLAISGLQSEDEADYYCAAWDDILNGEIFGGGTKVTVLG

In specific embodiments, Table 1 provides the heavy chain CDRs of each of the the A12, C2, E9, F1, F11, G1, H2, and H5 antibodies, cys-diabodies, and ScFv antibodies described herein. In specific embodiments, Table 2 provides the light chain CDRs of the A12, C2, E9, F1, F11, G1, H2, and H5 antibodies.

TABLE 1

Heavy Chain CDR Sequences of the A12, C2, E9, F1, F11, G1, H2, and H5 antibodies.
Heavy Chain CDR

| Antibody | CDR | SEQUENCE | SEQ ID |
|---|---|---|---|
| A12 | CDR-H1 | GFTFSSYAMS | 33 |
| | CDR-H2 | AISGSGGSTYYADSVKG | 34 |
| | CDR-H3 | SSSSWYRSYYFDY | 35 |
| C2 | CDR-H1 | GFTFSSYAMS | 36 |
| | CDR-H2 | AISGSGGSTYYADSVKG | 37 |
| | CDR-H3 | QHVGEQSRYFDY | 38 |
| E9 | CDR-H1 | GFTFSSYGMH | 39 |
| | CDR-H2 | AIGSSGGSTHDADTVKG | 40 |
| | CDR-H3 | DRARGFDY | 41 |
| F1 | CDR-H1 | GYTFTDYYMH | 42 |
| | CDR-H2 | WMNPNSGGTNYAQKFQG | 43 |
| | CDR-H3 | SHYWDS | 44 |
| F11 | CDR-H1 | RFTFSNYAMS | 45 |
| | CDR-H2 | AISGSGASTYYADSVKG | 46 |
| | CDR-H3 | LYGDYDY | 47 |
| G1 | CDR-H1 | GFTFSSYSMN | 48 |
| | CDR-H2 | SISSSSSYIYYADSVKG | 49 |
| | CDR-H3 | DLPSDDYGDYDYYYYGMDV | 50 |
| H2 | CDR-H1 | GFTFSTYAMS | 51 |
| | CDR-H2 | AISGSGGSTYYADSVKG | 52 |
| | CDR-H3 | EGGKWYYGMDV | 53 |
| H5 | CDR-H1 | GFTFSNYAMS | 54 |
| | CDR-H2 | AISGSGGSTYYADSVKG | 55 |
| | CDR-H3 | DRFRAAAY | 56 |

TABLE 2

Light Chain CDR Sequences of the A12, C2, E9, F1, F11, G1, H2, and H5 antibodies.
Light Chain CDR

| Antibody | CDR | SEQUENCE | SEQ ID |
|---|---|---|---|
| A12 | CDR-L1 | RGDSLRNYYAS | 57 |
| | CDR-L2 | GKNNRPS | 58 |
| | CDR-L3 | NSRDSSANQM | 59 |
| C2 | CDR-L1 | RASHSISSYVN | 60 |
| | CDR-L2 | AASYLPR | 61 |
| | CDR-L3 | QESYSTPYS | 62 |
| E9 | CDR-L1 | RASQGISSYLA | 63 |
| | CDR-L2 | GASSLQS | 64 |
| | CDR-L3 | QQLISYPLT | 65 |
| F1 | CDR-L1 | TGTSGDVGGYNYVS | 66 |
| | CDR-L2 | DVSNRPS | 67 |
| | CDR-L3 | TSYAGSRNLV | 68 |
| F11 | CDR-L1 | TGTSSDVGGYNYVS | 69 |
| | CDR-L2 | DVSNRPS | 70 |
| | CDR-L3 | SSYTSSSTLL | 71 |
| G1 | CDR-L1 | SGSSSNIASNSVK | 72 |
| | CDR-L2 | SDDQRPS | 73 |
| | CDR-L3 | AAWDDSLNAEV | 74 |
| H2 | CDR-L1 | QGDSLRSYYTN | 75 |
| | CDR-L2 | AKNKRPS | 76 |
| | CDR-L3 | NSRDSSGNYL | 77 |
| H5 | CDR-L1 | TGSSSNIGAGYDVH | 78 |
| | CDR-L2 | GNSNRPS | 79 |
| | CDR-L3 | AAWDDILNGEI | 80 |

Cancers

The anti-c-Met antibodies and antigen binding fragments thereof can be used to treat, diagnose, and determine the prognosis of various types of cancers. The cancers include, for example, carcinoma, lymphoma, blastoma, sarcoma and leukemia. More specific examples of cancer include squamous cell cancer, small-cell lung cancer, non-small cell lung cancer (NSCLC), non-Hodgkin's lymphoma, blastoma, gastrointestinal cancer, renal cancer, ovarian cancer, liver cancer, stomach cancer, bladder cancer, hepatoma, breast cancer, colon cancer, colorectal cancer, pancreatic cancer, endometrial carcinoma, salivary gland carcinoma, kidney cancer, liver cancer, prostate cancer, vulval cancer, thyroid cancer, hepatic carcinoma, and head and neck cancer. Particular groups of cancer include lung cancer (e.g., non-small cell lung carcinoma—NSCLC); or adenocarcinoma, which can, for example, be colorectal, pancreatic, or metastatic adenocarcinoma. Hematological cancers are also included.

Administrative Modalities

The antibodies and chemotherapeutic agents of the invention are administered to a subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In certain aspects, the antibodies and chemotherapeutic agents of the invention are administered to a subject with cancer. In certain aspects, the antibodies and chemotherapeutic agents of the invention are administered to a subject with breast cancer. In certain aspects, the antibodies and chemotherapeutic agents of the invention are administered to a subject with triple negative breast cancer. Intravenous or subcutaneous administration of the antibody is preferred.

Treatment Modalities

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth; (6) an increased patient survival rate; and (7) some relief from one or more symptoms associated with the disease or condition.

Positive therapeutic responses in any given disease or condition can be determined by standardized response criteria specific to that disease or condition. Tumor response can be assessed for changes in tumor morphology (i.e., overall tumor burden, tumor size, and the like) using screening techniques such as magnetic resonance imaging (Mill) scan, x-radiographic imaging, computed tomographic (CT) scan, bone scan imaging, endoscopy, and tumor biopsy sampling.

In addition to these positive therapeutic responses, the subject undergoing therapy may experience the beneficial effect of an improvement in the symptoms associated with the disease.

Such a response may persist for at least 4 to 8 weeks, or sometimes 6 to 8 weeks, following treatment according to the methods of the invention. Alternatively, an improvement in the disease may be categorized as being a partial response. By "partial response" is intended at least about a 50% decrease in all measurable tumor burden (i.e., the number of malignant cells present in the subject, or the measured bulk of tumor masses or the quantity of abnormal monoclonal protein) in the absence of new lesions, which may persist for 4 to 8 weeks, or 6 to 8 weeks.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects.

A "therapeutically effective amount" for tumor therapy may also be measured by its ability to stabilize the progression of disease. The ability of a compound to inhibit cancer may be evaluated in an animal model system predictive of efficacy in human tumors.

Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the anti-c-Met antibodies used in the present invention depend on the disease or condition to be treated and may be determined by the persons skilled in the art.

An exemplary, non-limiting range for a therapeutically effective amount of an anti-c-Met antibody used in the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg. In another embodiment, the antibody is administered in a dose of 1 mg/kg or more, such as a dose of from 1 to 20 mg/kg, e.g. a dose of from 5 to 20 mg/kg, e.g. a dose of 8 mg/kg.

A medical professional having ordinary skill in the art may readily determine and prescribe the effective amount of the pharmaceutical composition required. For example, a physician or a veterinarian could start doses of the medicament employed in the pharmaceutical composition at levels lower than that required in order to achieve the desired therapeutic effect and gradually increase the dosage until the desired effect is achieved.

In one embodiment, the anti-c-Met antibody is administered by infusion in a weekly dosage of from 10 to 500 mg/kg such as from 200 to 400 mg/kg. Such administration may be repeated, e.g., 1 to 8 times, such as 3 to 5 times. The administration may be performed by continuous infusion over a period of from 2 to 24 hours, such as from 2 to 12 hours.

In one embodiment, the anti-c-Met antibody is administered by slow continuous infusion over a long period, such as more than 24 hours, if required to reduce side effects including toxicity.

In one embodiment the anti-c-Met antibody is administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as from 2 to 12 hours. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the anti-c-Met antibody.

In a further embodiment, the anti-c-Met antibody is administered once weekly for 2 to 12 weeks, such as for 3 to 10 weeks, such as for 4 to 8 weeks.

In one embodiment, the anti-c-Met antibody is administered by maintenance therapy, such as, e.g., once a week for a period of 6 months or more.

In one embodiment, the anti-c-Met antibody is administered by a regimen including one infusion of an anti-c-Met antibody followed by an infusion of an anti-c-Met antibody conjugated to a radioisotope. The regimen may be repeated, e.g., 7 to 9 days later.

As non-limiting examples, treatment according to the present invention may be provided as a daily dosage of an antibody in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

Combination Therapy

In some embodiments the anti-c-Met antibody molecule thereof is used in combination with one or more additional therapeutic agents, e.g. a chemotherapeutic agent. Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and other inhibitors of proteins or enzymes known to be upregulated, over-expressed or activated in cancers, the inhibition of which downregulates cell replication.

In some embodiments, the antibodies of the invention can be used prior to, concurrent with, or after treatment with any of the chemotherapeutic agents described herein or known to the skilled artisan at this time or subsequently.

Efficacy of Methods Described Herein

In certain aspects of this invention, efficacy of anti-c-Met therapy is measured by decreased serum concentrations of tumor specific markers, increased overall survival time, decreased tumor size, cancer remission, decreased metastasis marker response, and decreased chemotherapy adverse affects.

In certain aspects of this invention, efficacy is measured with companion diagnostic methods and products. Companion diagnostic measurements can be made before, during, or after anti-c-Met treatment.

Diagnostics

In other embodiments, this disclosure relates to companion diagnostic methods and products. In one embodiment, the companion diagnostic method and products can be used to monitor the treatment of cancer, as described herein. In some embodiments, the companion diagnostic methods and products include molecular assays to measure levels of proteins, genes or specific genetic mutations. Such measurements can be used, for example, to predict whether anti-c-Met therapy will benefit a specific individual, to predict the effective dosage of anti-c-Met therapy, to monitor anti-c-Met therapy, adjust anti-c-Met therapy, tailor the anti-c-Met therapy to an individual, and track cancer progression and remission.

In some embodiments, the companion diagnostic can be used to monitor a combination therapy.

In some embodiments, the companion diagnostic can include an anti-c-Met antibody described herein.

In some embodiments, the companion diagnostic can be used before, during, or after anti-c-Met therapy.

Articles of Manufacture

In other embodiments, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

EXAMPLES

Example 1

Figure 5B:
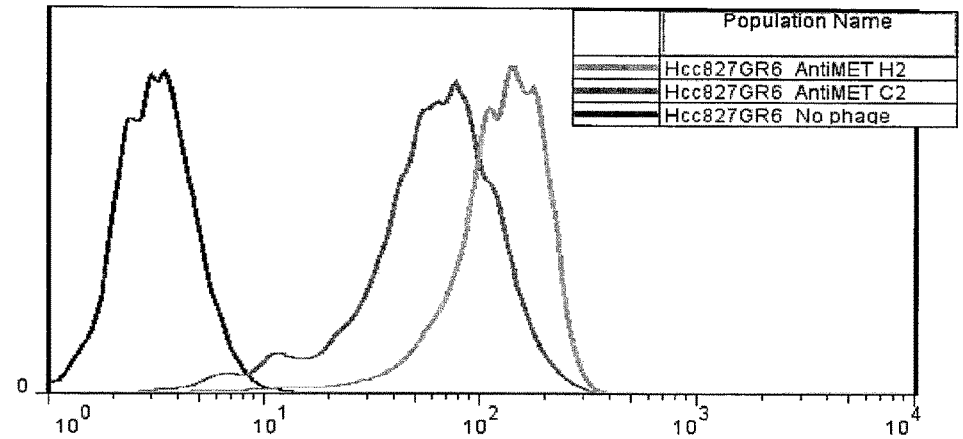
Figure 5C:
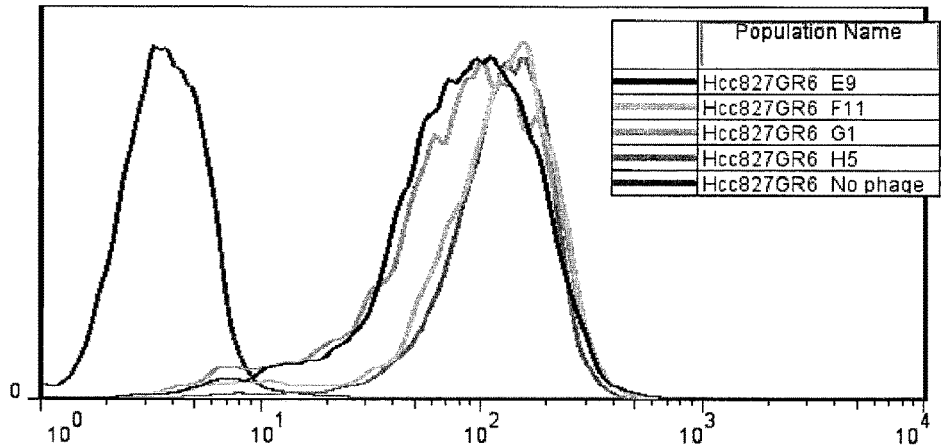

Three rounds of selections on human MET protein were performed which were successfully reformatted and purified 3 cys-diabodies. C2, H2 and H5 cys-diabodies were tested for cross-reactivity to mouse MET protein. Different cys-diabodies were coated to 96-well plate (milk or anti-EpCAM cys-diabody was used as negative control). Either mouse or human MET protein was applied to the coated cys-diabodies. Then the MET-hFc proteins were detected by anti-human Fc antibody. FIG. 5 shows the result of the ELISA. C2 and H5 cys-diabodies bind to only human MET, while H2 also cross reacts with mouse MET protein The affinities of these 3 diabodies were determined by flow cytometry using the Hcc827 GR6 cell line, which expresses high level MET.

These diabodies also show therapeutic effects on resistant cells with MET amplification. The parental cell line, Hcc827, was treated with the diabodies for 3 days, and the diabodies showed no effects on the growth of the parental line. The diabodies were also applied to the resistant cell line GR6 with or without 1 μM gefitinib. The H2 diabody showed the best inhibition effect, while the C2 and H5 diabodies only showed some inhibition at high concentrations.

These diabodies were also tested on other resistant cells without MET amplification (H1975 and H1650), and they show no effects on those cells. The H2 cys-diabody was site specifically conjugated with maleimide-DOTA and radiolabeled with 64Cu for PET imaging. Initial experiments showed targeting to both parental and resistant tumor.

Phage Library Panning.

The naive human scFv phage display library (the Sheets library) used for the panning was generated by JD Marks laboratory (Sheets et al. PNAS, 1998), which contains $6.7 \times 10^9$ members. The antigens used in the panning were two slightly different constructs based on the extracellular domain of human c-MET. The recombinant human c-MET Fc chimera protein was purchased from R&D Systems (Cat#: 358-MT/CF). Another human c-MET protein without Fc conjugation was purchased from Sino Biological Inc. (Cat#: 10692-H08H). For the first round of panning, 100 µg c-MET Fc chimera protein (R&D Systems) was coated onto an immunotube (Nunc) by overnight incubation in 2 mL PBS at 4 degrees. The immunotube was then washed and blocked with 2% milk in PBS at 37 degrees for 1 hour. After washing with PBS 3 times, $7 \times 10^{12}$ phage antibodies (generated from the Sheets library) in 2 mL 1% milk-PBS are added to the antigen-coated immunotube. After 2 hours of incubation at room temperature, the immunotube was washed 2 times with PBS. The binding phage antibodies were then eluted with 1 mL of 100 mM triethylamine for 8 minutes and neutralized with 0.5 mL of 1M Tris-HCl (pH 7.5). Half of the eluted phage was used to infect 10 mL exponentially growing *E. coli* TG1. Phage amplification and purification were carried out as previously described (Antibody Engineering Methods and Protocols, Benny K. C. Lo). Two more rounds of similar panning were performed with reduced amounts of c-MET protein from Sino Biological (30 µg for the 2nd round and 20 µg for the 3rd round), and with increased washing stringency (30 min of incubation with 0.05% PBS-Tween and multiple times of PBS washing). 93 clones were picked from the 3rd round panning and evaluated by phage ELISA.

Phage ELISA Screening of Individual Clones.

Phage antibodies were expressed from 93 clones from the 3rd round of panning as previously described (Antibody Engineering Methods and Protocols, Benny K. C. Lo). 50 µL of supernatant of the overnight culture was used for the ELISA. 0.5 µg of human c-MET Fc Chimera protein was used to coat each well. Blocking, washing and phage incubations are done as previously described (Antibody Engineering Methods and Protocols, Benny K. C. Lo). 100 µL of 1:2000 diluted HRP conjugated anti-M13 antibody (GE Healthcare, Cat#: 27-9421-01) was added to each well and incubated for 1 hour. After washing with PBS-Tween and PBS, 100 µL of 0.1 mg/mL ABTS (Sigma, A9941, Dissolved in 0.05M phosphate-citrate buffer, pH5.0, add 1/1000 of 50% H2O2 before use) was added to each well. The plate was then incubated at room temperature for 10 to 30 minutes before reading A405. The best binders were sequenced to identify unique binders.

Reformatting scFv into cys-diabody. ScFv (VH-Linker-VL) was reformatted into diabody by shortening the 15-aa linker to a 6-aa linker. The VH and VL fragments were amplified by PCR with new linker sequence fusing to the downstream of VH and upstream of VL. VH and VL PCR products and the pSYN1 vector were then assembled by isothermal DNA assembly following the previously published method (Gibson et al. Nature Methods, 2009). Myc tag, 6-his tag and a C-terminal cysteine were also fused to the C-terminal of the diabody in the process. All the coding sequences were confirmed by sequencing before protein expression.

Expression and purification of cys-diabody. The cys-diabody constructs were cloned into pSYN1 or pET22b vectors. The pSYN1 vector was transformed into TG1 bacteria while pET22b was transformed into Origami 2 (DE3) pLysS bacteria (Novagen) for protein expression. The H2 cys-diabody exhibitied better yield with pSYN1 vector and TG1 strain, while others exhibited better yield with the pET22b vector and Origami 2 (DE3) pLysS. The bacteria cells were grown at 37 degrees until O.D. 600 reached 1. The expression was then induced by addition of 0.5 mM to 1 mM IPTG at 20 degrees overnight. The bacteria cells were then collected and lysed by bugbuster master mix (EMD Millipore, 71456), with 1 mM phenylmethylsulfonyl fluoride (PMSF) and 20 mM imidazole. The soluble fraction was then collected after centrifugation and filtered through 0.22 µm filter before loading to a HisTrap HP column (GE Healthcare, 17-5247-01). The 6-his tagged cys-diabodies were then eluted with imidazole, desalted with PD-10 column (GE Healthcare, 17-0851-01), and dialyzed against PBS.

Flow Cytometry.

For phage antibodies, flow cytometry was used to confirm their binding to c-MET expressing cells. Bacteria culture containing phage was concentrated 30 times into PBS according to published method (Antibody Engineering Methods and Protocols, Benny K. C. Lo). $2 \sim 5 \times 10^5$ c-MET positive Hcc827 or Hcc827-GR6 cells (Engelman et. al, Science, 2007) were incubated with 100 ul concentrated phage and 30 ul 4% milk-PBS on ice for 1 hour. Cells were then washed using flow buffer (PBS, 1% FBS, 2 mM EDTA), and the binding phage antibodies were detected by FITC conjugated anti-M13 monoclonal antibody (Santa Cruz Biotechnology, Cat# sc-53005 Fitc).

The affinities of the cys-diabodies were evaluated by flow cytometry. Serial diluted cys-diabodies were incubated with Hcc827-GR6 cells at 4 degrees for 2 hours. The cys-diabodies were detected with 1/100 mouse anti-c-Myc antibody (Sigma, Cat# M4439) and stained with 1/100 PE or FITC conjugated goat anti mouse IgG polyclonal antibody (Jackson ImmunoResearch) in flow buffer.

Cell Growth Assays.

Cell growth and inhibition were evaluated by MTS assay. The MTS assay was based on the ability of live cells to convert 3-(4,5-dimethylthiazol-2-yl)-5-(3-carboxymethoxyphenyl)-2-(4-sulfophenyl)-2H-tetrazolium (MTS) to formazan. The quantity of formazan product was measured by 500 nm absorbance, which is proportional to the number of living cells in culture. The assay was performed with the CellTiter96 AQueous Assay Kit from Promega (Cat# G5421), according to the recommended protocol. $2 \times 10^4$ cells were seeded in each well of the 96-well plates and treated with different combination of antibodies and drugs for 3 days before the MTS assay. Each combination of cell line and drug and antibody treatment was set up in at least 4 replicate wells. And the results were normalized to the cells treated with media only.

Anti-MET ELISA.

1 µg of purified anti-MET cys-diabodies in 100 µL PBS were used to coat each well at 4 degree overnight. Anti-EpCAM cys-diabody or 2% milk-PBS were used for negative controls. The overnight coated plate was then washed with PBS and blocked with 2% milk-PBS at 37 degree for 2 hours. The plate was then washed with PBS before adding 0.1 µg human or mouse MET-hIgG Fc fusion protein (purchased from Sino Biological Inc.) in 100 µL, 2% milk-PBS to each well. The plate was incubated at room temperature for 1.5 hours, and then washed with PBS-Tween and PBS. The captured human or mouse MET-hIgG Fc were detected with alkaline phosphatase conjugated goat anti-human IgG.

Cell Lines and Tumor Models.

Hcc827 parental cells and the gefitinib resistant Hcc827-GR6 cells were obtained from Jeffrey A. Engelman's lab. The parental Hcc827 cells were maintained with RPMI 1640 media supplemented with 10% FBS (fetal bovine serum, Invitrogen), 1% sodium pyruvate (Invitrogen) and 1% penicillin-streptomycin (Invitrogen). The Hcc827-GR6 cells were maintained with RPMI1640 media supplemented with 10% FBS, 1% sodium pyruvate, 1% penicillin-streptomycin and 100 nM gefitinib (Santa Cruz biotechnology, Cat#: sc-202166). MKN45 cells (Japanese Collection of Research Bioresources cell bank) were maintained in RPMI 1640 media supplemented with 10% FBS. C6 rat glioma cells were maintained in deficient DME high glucose media (Irvine Scientific) supplemented with 10% FBS, 1% penicillin-streptomycin and 2 mM L-glutamine. Female SCID mice (Jackson Laboratory) were injected subcutaneously into the left or right shoulders with cells ($2$-$4 \times 10^6$) in growth media: 50% Matrigel (BD Biosciences). The tumors were allowed to develop for 2-5 weeks before imaging. All animal studies were carried out under a protocol approved by the Chancellor's Animal Research Committee of the University of California in Los Angeles.

Radiolabeling of Cys-Diabodies.

Antibody fragments were first dialyzed into metal free PBS (0.5-2 mg/mL). Cys-diabodies were treated with 15-20 fold excess of TCEP (tris(2-carboxyethyl)phosphine) for approximately 2 hours at room temperature to reduce the C-terminal disulfide bond into free thiols. 20-fold excess Deferoxamine-maleimide (Macrocyclics, Cat#: B-772) was then added to the reaction to site-specifically label the C-terminal cysteine. After 3-4 hours at room temperature, the site-specifically labeled cys-diabody-maleimide-DFO was purified with PD-10 column (GE Healthcare). Zr-89 oxalic acid solution (Washington University) was neutralized with $Na_2CO_3$ (2M) and HEPES buffer (1M, pH 7.0), and then reacted with the cys-diabody-meleimide-DFO at room temperature for 1 hour. The Zr-89 labeled antibody fragments were then purified with PD-10 column. The labeling efficiency and radio-chemical purity were determined by ITLC (instant thin-layer chromatography). To assess immunoreactivity, a small amount of radiolabeled antibody fragment (~0.2 ng) was incubated with excess antigen positive MKN45 cells (~100 million cells in 0.5 mL PBS with 1% FBS) for 1 hour at room temperature, after which the cells were pelleted and washed with 1 mL PBS twice. The radioactivity of the combined and supernatant and cell pellet was measured by a Wizard 3' 1480 Automatic Gamma Counter (Perkin-Elmer, Covina, Calif.). The immunoreactivity was calculated by dividing the radioactivity in the cell pellet with the total radioactivity of supernatant and cell pellet. The antigen negative C6 cells were also used as negative control.

Small Animal PET Imaging and Ex-Vivo Biodistribution Studies.

Tumor bearing mice were injected via tail vein with approximately 18-25 µg of Zr-89 labeled cys-diabody in PBS. The 10-minute micro-PET scans were performed at 4 and 20 hours post injection with an Inveon PET Scanner (Siemens). A 10-minute CT scan was performed after each micro-PET scan to provide anatomical reference, with a MicroCAT II Scanner (Concorde Microsystems). The mice were anesthetized with 2% isoflurane during the scanning process. Micro-PET images were reconstructed using a filtered backprojection algorithm, and analyzed with AMIDE software. Ex-vivo biodistribution studies were performed after the final imaging time point. Organs, tumors and blood were harvested and weighed, and the radioactivities were measured with Wizard 3' 1480 Automatic Gamma Counter. The percent injected dose per gram of tissue (% ID/g) was calculated after decay correction to evaluate the uptake level in each organ.

Results. The naive human scFv library with $6.7 \times 10^9$ members (Sheets library) was panned against human c-MET recombinant protein. The amount of antigen used, the input and output phage number and the recovery for each round is shown in Table 3.

TABLE 3

Results of 3 rounds of anti-cMET panning

| | Antigen used | Input phage | Output phage | Recovery |
|---|---|---|---|---|
| Round 1 | 100 µg c-MET Fc chimera (R&D) | $6.8 \times 10^{12}$ cfu | $3.6 \times 10^8$ cfu | $5 \times 10^{-5}$ |
| Round 2 | 30 µg c-MET (Sino Biological) | $2 \times 10^{13}$ cfu | $7 \times 10^6$ cuf | $3.5 \times 10^{-7}$ |
| Round 3 | 20 µg c-MET (Sino Biological) | $1 \times 10^{14}$ cfu | $5 \times 10^6$ cfu | $5 \times 10^{-8}$ |

93 clones were randomly picked after 3 rounds of panning. The phage-containing supernatant was used for phage ELISA. Top 64 clones with highest A405 signal were sequenced, among which 19 distinctive clones with different sequences were identified. These distinctive clones were then tested for binding to cell surface MET by phage flow experiments. 8 of these clones show good binding to cell surface MET and were selected for the subsequent purification and characterizations. The phage flow results of the 8 best clones are shown in FIG. 5.

H2, C2, and H5 cys-diabodies were expressed in higher levels than other clones. H2 cys-diabody was expressed well with pSYN1 vector in TG1 bacteria, with the yield of 3 mg per liter. C2 and H5 cys-diabodies were expressed with pET22b vector in Origami-2 (DE3) pLysS bacteria, with the yield of 0.6 mg per liter and 1 mg per liter respectively.

Figure 6A:
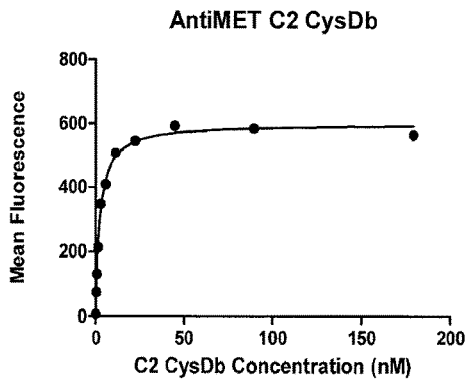
FIG. 6A-FIG. 6C depicts the binding curves of C2, H2 and H5 cys-diabodies on Hcc827-GR6 cells.
Figure 6B:
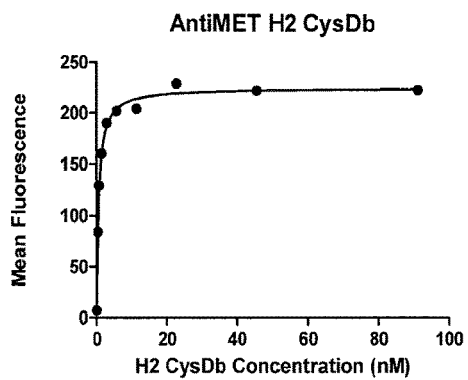
Figure 6C:
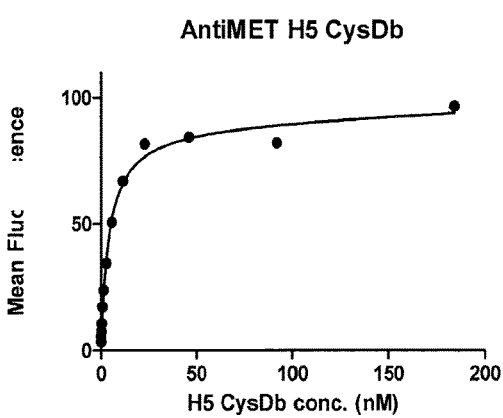
Figure 8A:
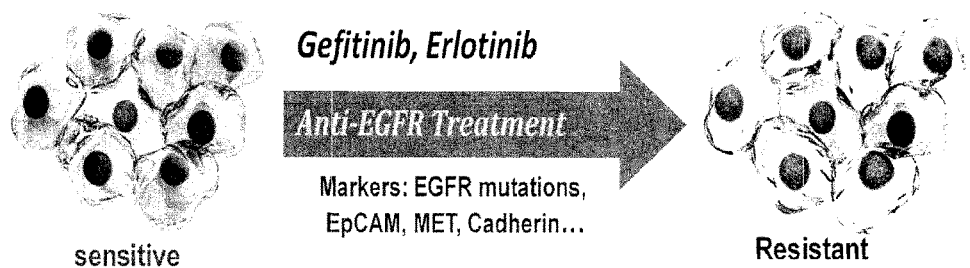
FIG. 8A-FIG. 8D depicts the use of cys-diabodies for use in treatment and detection of disease and the use of antibody fragments for nano-applications.
Figure 8B:
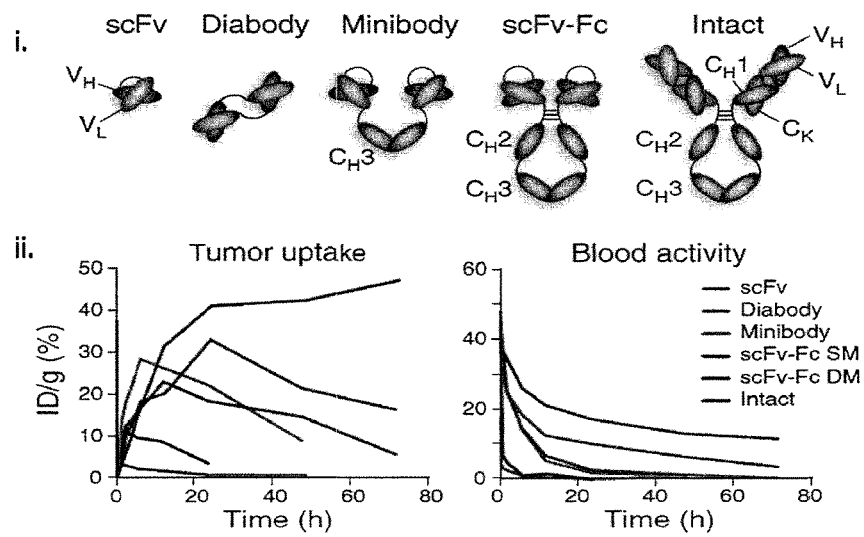
Figure 8C:
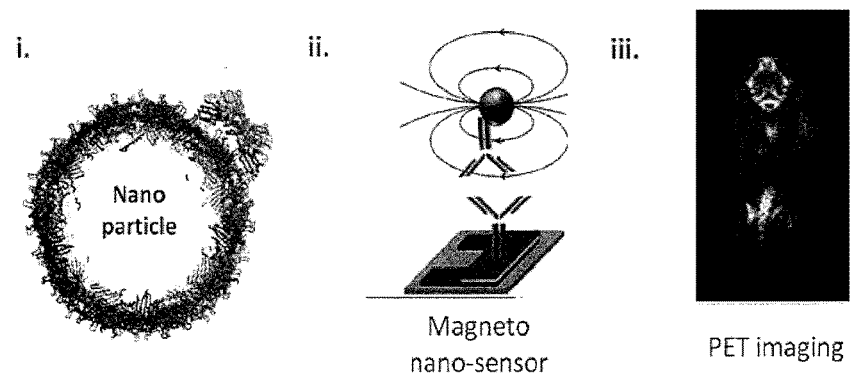
Figure 8D:
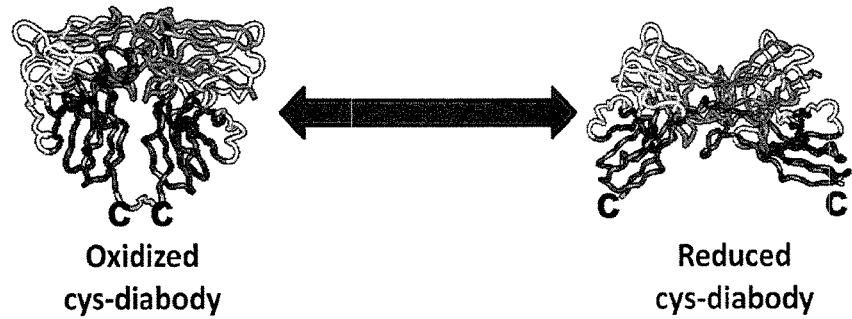
Figure 9:
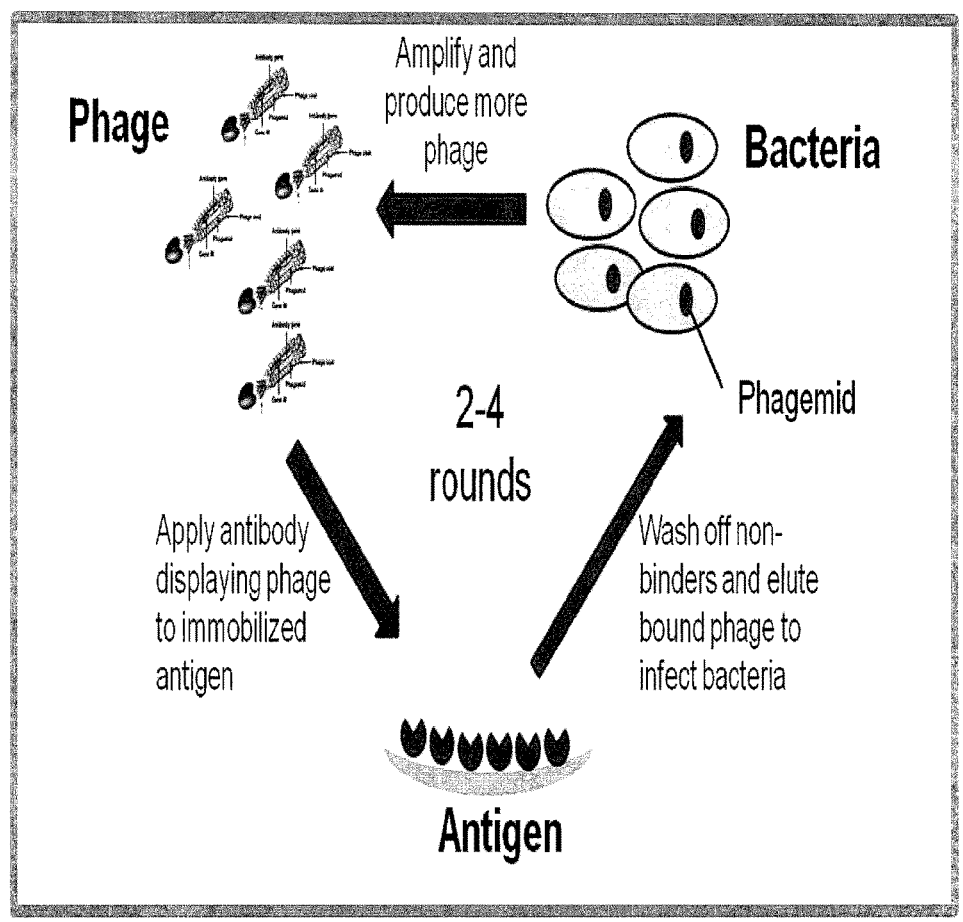
FIG. 9 depicts the scheme of phage display technology and detection of novel antibodies from a phage display library.
Figure 10:
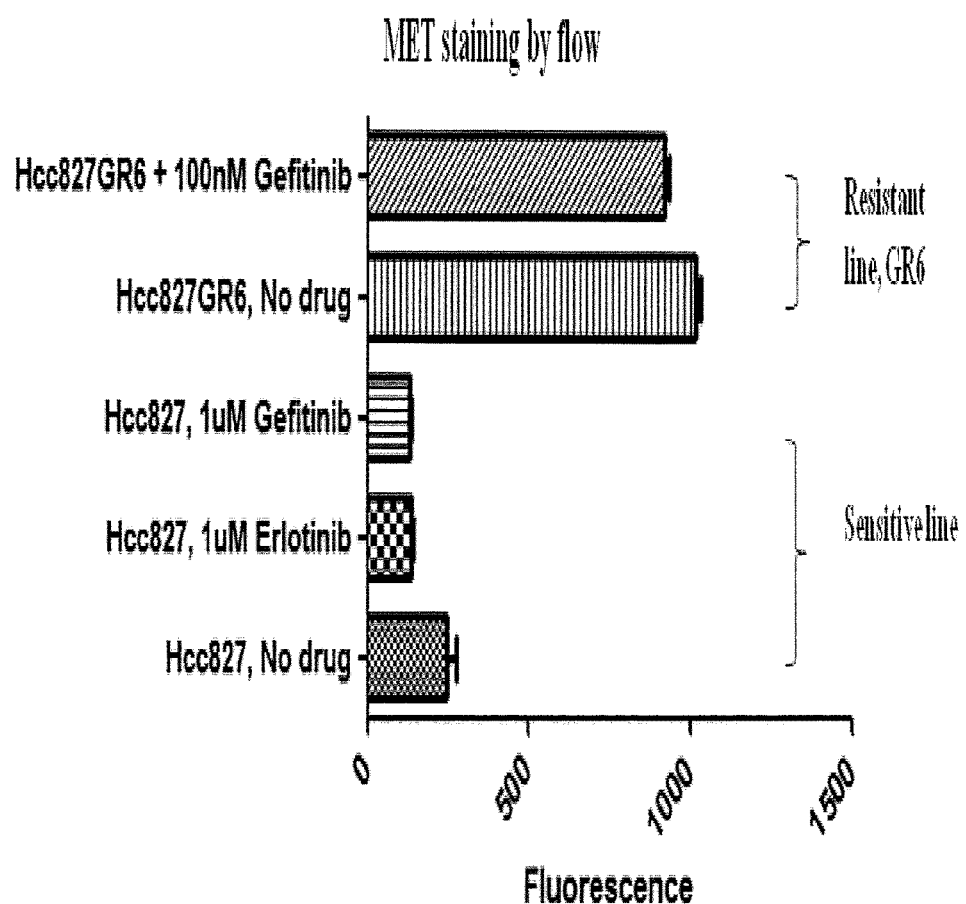
FIG. 10 depicts MET staining by flow cytometry.
Figure 11:
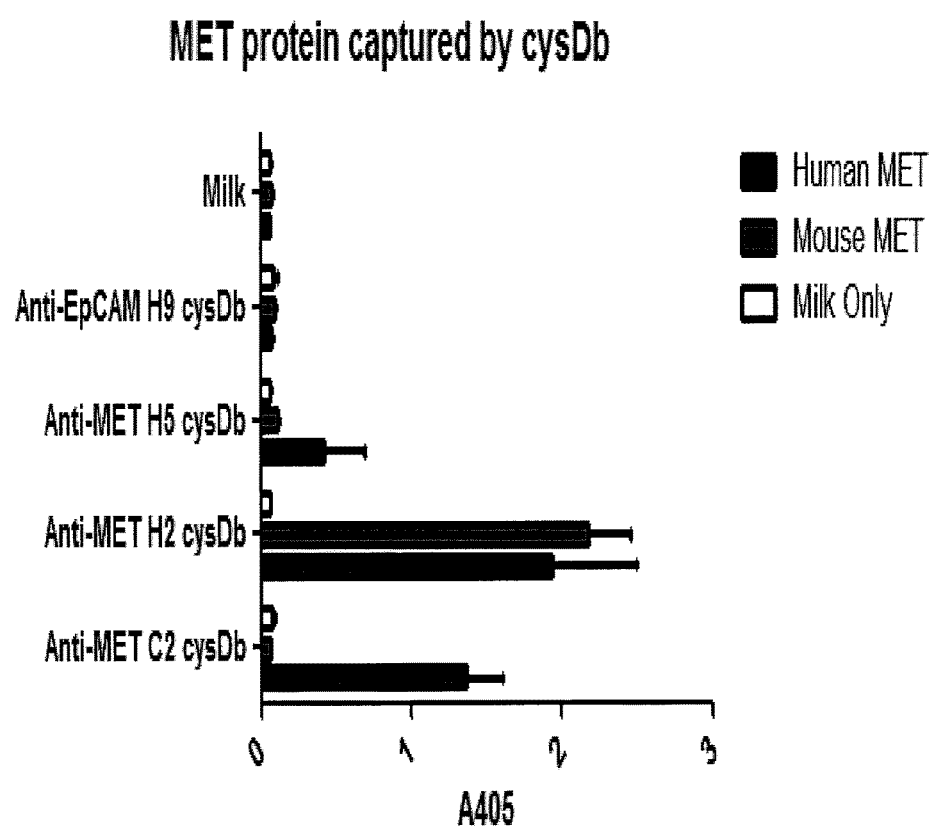
FIG. 11 depicts the amount of MET protein captured by the anti-c-Met cys-diabody.
Figure 12A:
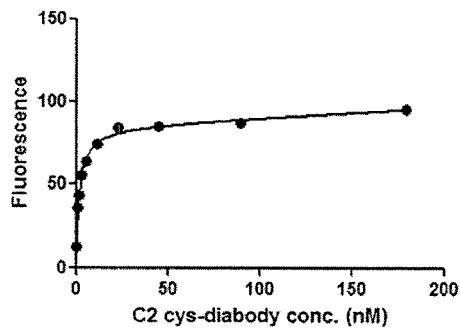
FIG. 12A-FIG. 12C depicts anti-c-Met cys-diabody binding curves.
Figure 12B:
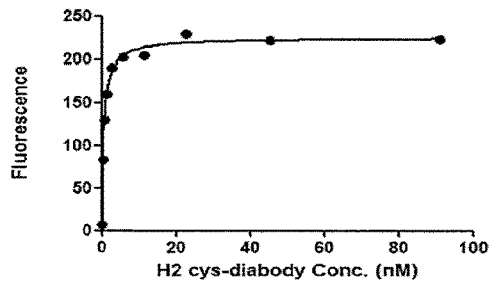
Figure 12C:
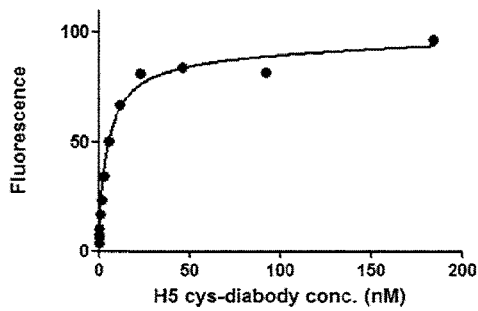
Figure 13:
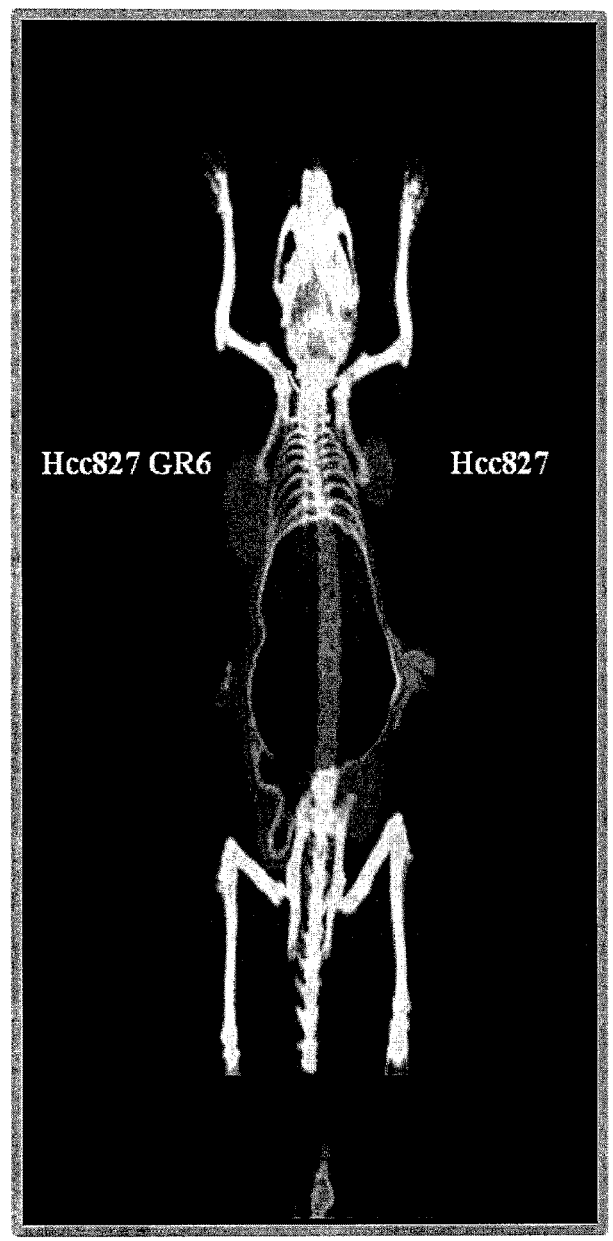
FIG. 13 depicts in vivo imaging using a anti-c-Met cys-diabody scanned at 4 hours post injection. The image was processed with 2 mm Gaussian filter.
Figure 14:
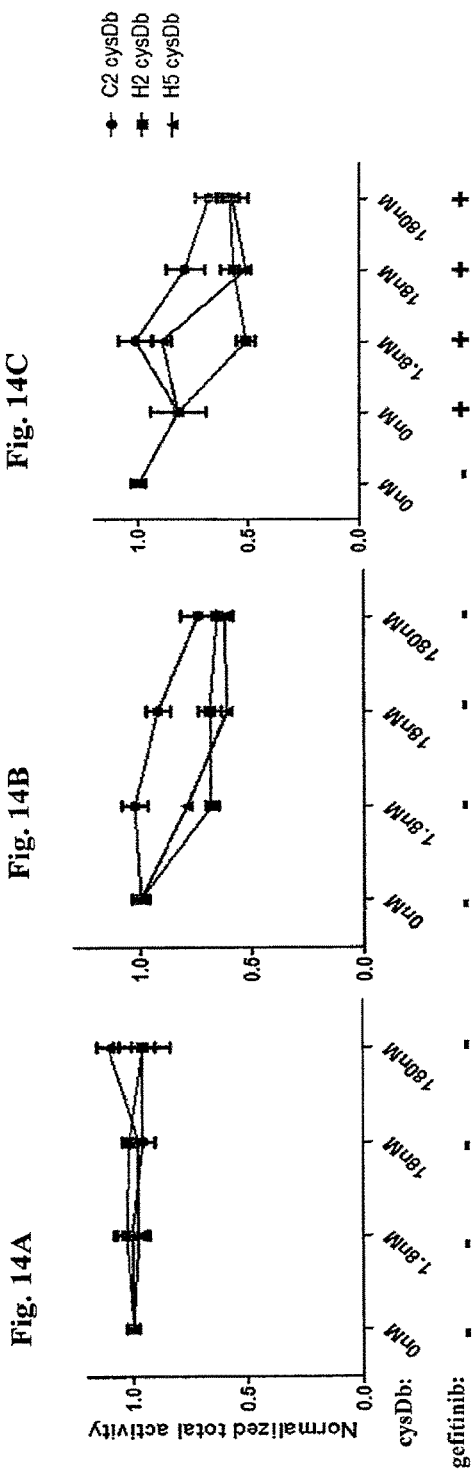
FIG. 14A-FIG. 14C depicts the normalized total activities of anti-c-Met cys-diabodies.
Figure 15:
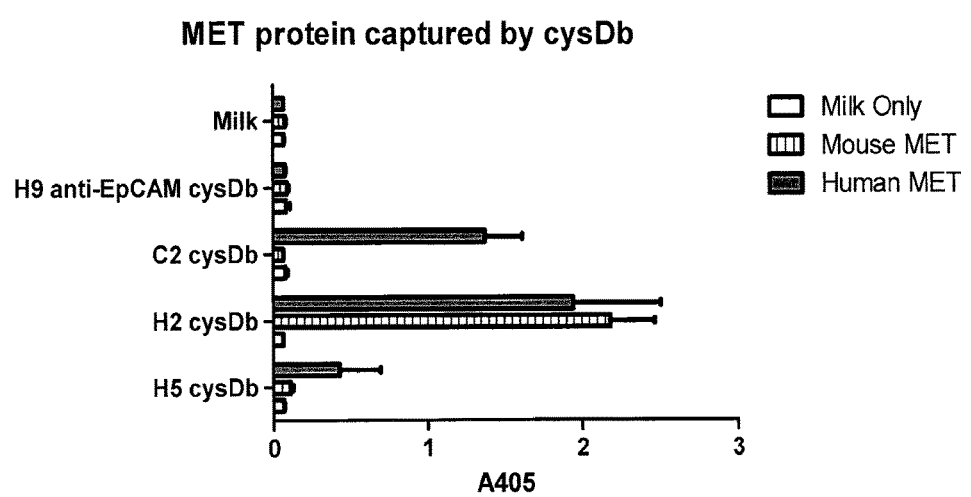
FIG. 15 depicts ELISA results of the C2, H2, and H5 cys-diabodies to human mouse MET proteins.
Figure 16A:
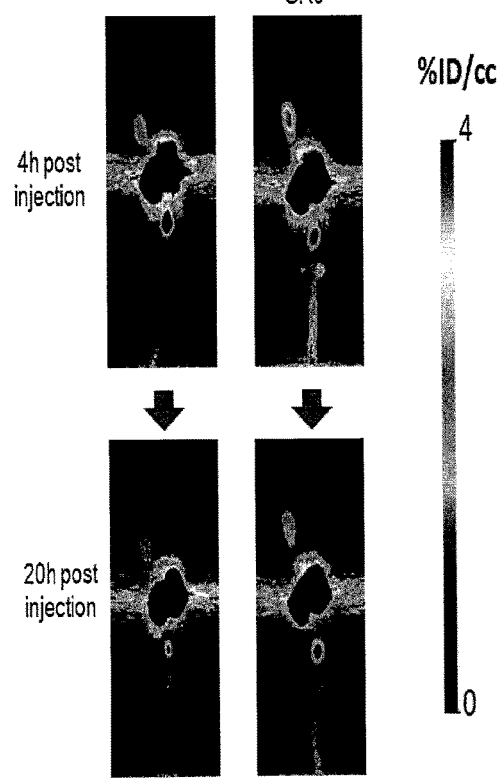
FIG. 16A-FIG. 16B depicts PET scans and ex vivo biodistribution studies that show significant difference between the Hcc827-GR6 and the Hcc827 parental tumors.
Figure 16B:
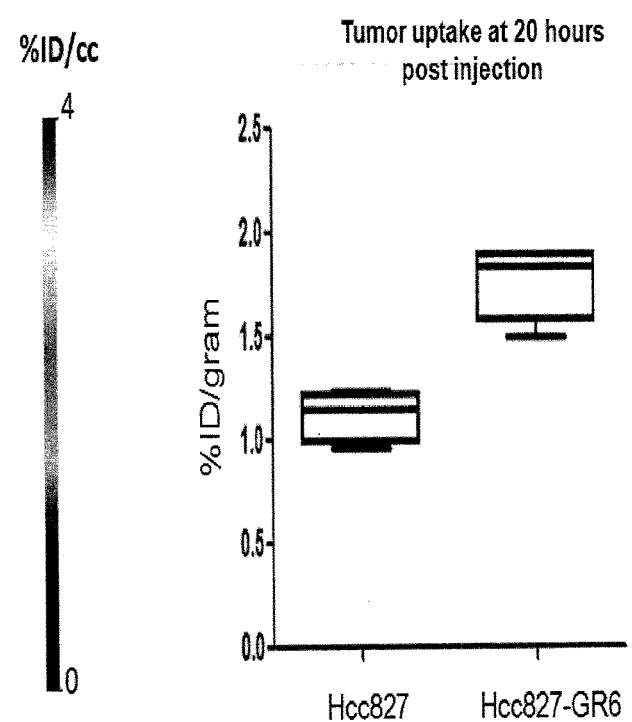

The affinity of these 3 cys-diabodies were evaluated by flow cytometry. The concentrations of the purified proteins were determined by their A280, measured with Nanodrop 2000 (Thermal Scientific), and their calculated extinction coefficient (ProtParam tool, expasy.org). The binding curve was fitted with one-site total binding model by GraphPad Prism. The estimated dissociation constants were listed in Table 4 and the fitted binding curves are shown in FIG. 6.

TABLE 4

Estimated dissociation constants and standard errors of the C2, H2 and H5 cys-diabodies

| | Kd (dissociation constant) | Std. Error |
|---|---|---|
| C2 cys-diabody | 2.4 nM | 0.2 nM |
| H2 cys-diabody | 0.61 nM | 0.07 nM |
| H5 cys-diabody | 4.6 nM | 0.6 nM |

Different cell lines were treated with C2, H2 or H5 cys-diabodies at different concentrations with or without 1 micromolar of gefitinib for 3 days, and then the cell growth was evaluated with MTS assay. While H2 cys-diabody shows inhibition effect of the MET amplified, drug resistant Hcc827-GR6 cells with or without gefitinib, C2 cys-diabody actually protects the sensitive Hcc827 cells from gefitinib inhibition. H5 cys-diabody also shows inhibition of the resistant cells at higher concentration. All three cys-diabodies show no effects on the parental Hcc827 cells without gefitinib. These results are shown in FIG. 7.

Anti-MET ELISA to Test Cross Reactivity of Cys-Diabodies.

C2, H2 and H5 cys-diabodies were used to coat 96-well ELISA plate to capture human or mouse MET-hIgG Fc fusion protein. The human IgG Fc on the fusion protein was detected with alkaline phosphatase conjugated goat anti-human IgG. The results in FIG. 4 show H2 cys-diabody can bind to both human and mouse MET protein, while C2 and H5 cys-diabodies show minimal cross reactivity to the mouse MET. Anti-EpCAM H9 cys-diabody or 2% milk-PBS were used as negative controls.

Anti-MET PET Imaging Using Zr-89 Labeled 112 Cys-Diabody.

SCID mice were injected with either MET positive Hcc827 parental cells or Hcc827-GR6 resistant cells to the left shoulders, and C6 cells to the right shoulders as negative controls. H2 cys-diabody was site-specifically labeled with maleimide-DFO, and then radio-labeled with Zr-89. The radioactive H2 cys-diabody was then injected to the tumor bearing SCID mice through tail vein. FIG. 5A shows two SCID mice with similar-sized MET positive tumors (Hcc827: 212 mg; Hcc827-GR6: 262 mg) scanned at 4 hours and 20 hours post injection. FIG. 5B shows ex-vivo biodistribution study. The result shows significant difference in tumor uptake for Hcc827 and Hcc827-GR6 (n=4, P=0.0013). The difference in tumor uptake level (Hcc827: 1.1±0.1% ID/gram; Hcc827-GR6: 1.8±0.2% ID/gram) agrees with the difference in MET expression level (Hcc827: $6.7 \times 10^4$; Hcc827-GR6: $2.6 \times 10^5$).

Example 2

MET over-expression is a known mechanism for acquired gefitinib resistance. J. Engelman's lab (Harvard) obtained several gefitinib resistant cell lines from Hcc827 cells by prolonged gefitinib treatment (Engelman et al. 2007, Science). These cells showed increased MET copy number and expression level. One of these cell lines, the GR6 cell line, was obtained and a higher MET expression level compared to Hcc827 parental cells by flow cytometry was determined. It was also found that the parental Hcc827 cells down-regulate their MET level by ~50% after 18 hours of drug treatment. Accordingly, MET can be used as a resistance marker and a response marker.

Three rounds of selections on human MET protein were performed, and three cys-diabodies were reformatted and purified (the C2, H2 and H5 cys-diabodies). The C2, H2 and H5 cys-diabodies were tested for cross-reactivity to mouse MET protein. Different cys-diabodies were coated to 96-well plate (milk or anti-EpCAM cys-diabody was used as negative control). Either mouse or human MET protein was applied to the coated cys-diabodies. Then the MET-hFc proteins were detected by anti-human Fc antibody. C2 and H5 cys-diabodies were shown to bind to only human MET, while H2 was shown to also cross react with mouse MET protein.

The affinities of these 3 diabodies were determined by flow cytometry using the Hcc827 GR6 cell line, which expresses high level MET.

These diabodies also show therapeutic effects on resistant cells with MET amplification. The parental cell line, Hcc827, was treated with the diabodies for 3 days, and the diabodies show no effects on the growth of the parental line at all. The diabodies were also applied to the resistant cell line GR6 with or without 1 μM gefitinib, and H2 showed the greatest inhibition effect, while C2 and H5 show inhibition only at high concentrations.

These diabodies were also applied to other resistant cells without MET amplification (H1975 and H1650). The diabodies had no effect on such cells. (Data not shown). The H2 cys-diabody was site specifically conjugated with maleimide-DOTA and radiolabeled with $^{64}$Cu for PET imaging. Initial experiments showed targeting to both parental and resistant tumor.

Each publication, patent application, patent, and other reference cited herein is incorporated by reference in its entirety to the extent that it is not inconsistent with the present disclosure. In particular, all publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. An isolated human anti-c-Met antibody comprising a human heavy chain variable domain and a human light chain variable domain, wherein the anti-c-Met antibody is selected from a group consisting of:
   an anti-c-Met antibody comprising a human heavy chain variable domain comprising the amino acid sequence of SEQ ID NO:1 and a human light chain variable domain comprising the amino acid sequence of SEQ ID NO:9;
   an anti-c-Met antibody comprising a human heavy chain variable domain comprising the amino acid sequence of SEQ ID NO:2 and a human light chain variable domain comprising the amino acid sequence of SEQ ID NO:10;
   an anti-c-Met antibody comprising a human heavy chain variable domain comprising the amino acid sequence of SEQ ID NO:3 and a human light chain variable domain comprising the amino acid sequence of SEQ ID NO:11;
   an anti-c-Met antibody comprising a human heavy chain variable domain comprising the amino acid sequence of SEQ ID NO:4 and a human light chain variable domain comprising the amino acid sequence of SEQ ID NO:12;
   an anti-c-Met antibody comprising a human heavy chain variable domain comprising the amino acid sequence of SEQ ID NO:5 and a human light chain variable domain comprising the amino acid sequence of SEQ ID NO:13;
   an anti-c-Met antibody comprising a human heavy chain variable domain comprising the amino acid sequence of SEQ ID NO:6 and a human light chain variable domain comprising the amino acid sequence of SEQ ID NO:14;
   an anti-c-Met antibody comprising a human heavy chain variable domain comprising the amino acid sequence of SEQ ID NO:7 and a human light chain variable domain comprising the amino acid sequence of SEQ ID NO:15; and
   an anti-c-Met antibody comprising a human heavy chain variable domain comprising the amino acid sequence of SEQ ID NO:8 and a human light chain variable domain comprising the amino acid sequence of SEQ ID NO:16.

2. The isolated human anti-c-Met antibody of claim 1, wherein the antibody or antigen binding fragment thereof is a diabody.

3. The isolated human anti-c-Met antibody of claim 2, wherein the diabody is a cys-diabody.

4. The isolated human anti-c-Met antibody of claim 3, wherein the cys-diabody comprises the amino acid sequence SEQ ID NOS:17, 18, 19, 20, 21, 22, 23, or 24.

5. The isolated human anti-c-Met antibody of claim 1, wherein the antibody is a single-chain variable fragment (ScFv).

6. The isolated human anti-c-Met antibody of claim 5, wherein the ScFv comprises the amino acid sequence SEQ ID NOS:25, 26, 27, 28, 29, 30, 31, or 32.

7. The isolated human anti-c-Met antibody of claim 1, wherein the antibody or antigen binding fragment thereof is a minibody or a triabody.

8. The isolated human anti-c-Met antibody of claim 1, wherein the antibody or antigen binding fragment thereof is a fully human antibody.

9. The isolated human anti-c-Met antibody of claim 1, wherein the antibody or antigen binding fragment thereof is chimeric.

10. The isolated human anti-c-Met antibody of claim 1, wherein the antibody or antigen binding fragment thereof is conjugated to a cytotoxic agent.

11. The isolated human anti-c-Met antibody of claim 10, wherein the cytotoxic agent is a chemotherapeutic agent.

12. The isolated human anti-c-Met antibody of claim 11, wherein the chemotherapeutic agent is selected from the group consisting of gemcitabine, carboplatin, taxol, and paclitaxel.

13. The isolated human anti-c-Met antibody of claim 1, wherein the antibody or antigen binding fragment thereof is conjugated to a fluorescent molecule.

14. The isolated human anti-c-Met antibody of claim 1, wherein the antibody or antigen binding fragment thereof is radiolabeled.

15. The isolated human anti-c-Met antibody of claim 14, wherein the radiolabel is an iodine radiolabel.

16. The isolated human anti-c-Met antibody of claim 1, wherein the antibody or antigen binding fragment thereof has an affinity between 0.3 nM and 9 nM to c-Met.

17. A pharmaceutical composition comprising the antibody isolated human anti-c-Met antibody of claim 1 and a physiologically acceptable carrier.

18. The pharmaceutical composition of claim 17, wherein the composition is administered by parenteral, subcutaneous, intraperitoneal, intrapulmonary, or intranasal administration.

19. The pharmaceutical composition of claim 18, wherein the parenteral administration comprises intramuscular, intravenous, intraarterial, intraperitoneal, or subcutaneous administration.

20. The pharmaceutical composition of claim 17, wherein the composition is co-administered with a cytotoxic agent.

21. A method of diagnosing a c-Met expressing cancer in a subject comprising administering an antibody conjugate to the subject and detecting an overexpression of c-Met in the subject,
   wherein the antibody conjugate comprises the antibody of claim 1 and a detectable label,
   wherein overexpression of c-Met in the subject is indicative of the presence of the cancer.

22. A method of treating a c-Met expressing patient for cancer, the method comprising administering to the patient an effective amount of the anti-c-Met antibody of claim 1.

23. The method of claim 22, further comprising administering to the patient an effective amount of at least one additional anti-cancer agent.

24. The method of claim 22, wherein the at least one additional anti-cancer agent is selected from the group consisting of platinum-based chemotherapy drugs, taxanes, tyrosine kinase inhibitors, anti-EGFR antibodies, anti-ErbB2 antibodies, and combinations thereof.

25. The method of claim 22, wherein the patient is human or mammal.

26. The isolated antibody of claim 1, wherein the anti-cMet antibody has a 6-histidine tag.

27. The isolated antibody of claim 26, wherein the 6-histidine tag is enzymatically cleaved off after purification of the antibody.

28. The isolated antibody of claim 1, wherein the anti-cMet antibody has a Myc tag.

29. The isolated antibody of claim 28, wherein the Myc tag is enzymatically cleaved off after purification of the antibody.

30. The isolated antibody of claim 1, wherein the anti-cMet antibody has a Myc tag and a 6-Histidine tag.

31. The isolated antibody of claim 30, wherein the Myc tag and 6-Histidine tag is enzymatically cleaved off after purification of the antibody.

32. The isolated antibody of claim 30, wherein the anti-cMet antibody has a linker, a Myc tag, and a 6-Histidine tag, wherein the sequence of the linker, the Myc tag, and the 6-Histidine tag comprises SEQ ID NO: 81.

33. The anti-c-Met diabody of claim 2 wherein the heavy chain variable domain sequence and light chain variable domain sequence are linked by a linker comprising SEQ ID NO: 82.

34. The anti-c-Met scFv antibody of claim 5 wherein the heavy chain variable domain sequence and light chain variable domain sequence are linked by a linker comprising SEQ ID NO: 81.

35. The isolated antibody of claim 1, wherein the anti-cMet antibody has one or more terminal cysteines.

36. The isolated antibody of claim 35, wherein one or more terminal cysteines is labeled with a detectable molecule comprising a fluorophore, a radio label, a luminescent label, a chemoluminescent label, or a spin label.

37. The method of claim 21, wherein the cancer is lung cancer.

38. The method of claim 37 wherein the lung cancer is non-small cell lung cancer.

* * * * *

SEQUENCE LISTING

```
<160> NUMBER OF SEQ ID NOS: 83

<210> SEQ ID NO 1
<211> LENGTH: 122
<212> TYPE: PRT
<213> ORGANISM: Artificial Sequence
<220> FEATURE:
<223> OTHER INFORMATION: A12 heavy chain variable domain sequence

<400> SEQUENCE: 1

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ser Trp Tyr Arg Ser Tyr Tyr Phe Asp Tyr Trp
                100                 105                 110

Gly Gln Gly Thr Leu Val Thr Val Ser Ser
            115                 120

<210> SEQ ID NO 2
<211> LENGTH: 121
<212> TYPE: PRT
<213> ORGANISM: Artificial Sequence
<220> FEATURE:
<223> OTHER INFORMATION: C2 heavy chain variable domain

<400> SEQUENCE: 2

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gln His Val Gly Glu Gln Ser Arg Tyr Phe Asp Tyr Trp Gly
                100                 105                 110

Gln Gly Thr Leu Val Thr Val Ser Ser
            115                 120

<210> SEQ ID NO 3
<211> LENGTH: 117
<212> TYPE: PRT
<213> ORGANISM: Artificial Sequence
<220> FEATURE:
<223> OTHER INFORMATION: E9 heavy chain variable domain sequence

<400> SEQUENCE: 3

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ser Ala Ile Gly Ser Ser Gly Ser Thr His Asp Ala Asp Thr Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Asp Arg Ala Arg Gly Phe Asp Tyr Trp Gly Gln Gly Thr Leu
            100                 105                 110

Val Thr Val Ser Ser
            115

<210> SEQ ID NO 4
<211> LENGTH: 115
<212> TYPE: PRT
<213> ORGANISM: Artificial Sequence
<220> FEATURE:
<223> OTHER INFORMATION: F1 heavy chain variable domain sequence

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Glu Gly Leu Glu Trp Met
        35                  40                  45

Gly Trp Met Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser His Tyr Trp Asp Ser Trp Ser Pro Gly Thr Leu Val Thr
            100                 105                 110

Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: F11 heavy chain variable domain sequence

<400> SEQUENCE: 5

Gln Val Gln Leu Gln Glu Ser Gly Gly Gly Leu Leu Gln Pro Gly Gly
1               5                   10                  15

Ser Leu Arg Leu Ser Cys Ala Ala Ser Arg Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Asn Leu Tyr Gly Asp Tyr Asp Tyr Trp Gly Gln Gly Thr Leu Val
            100                 105                 110

Thr Val Ser Ser
        115

<210> SEQ ID NO 6
<211> LENGTH: 128
<212> TYPE: PRT
<213> ORGANISM: Artificial Sequence
```

```
<220> FEATURE:
<223> OTHER INFORMATION: G1 heavy chain variable domain sequence

<400> SEQUENCE: 6

Gln Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Ser Asp Asp Tyr Gly Asp Tyr Asp Tyr Tyr Tyr
            100                 105                 110

Tyr Gly Met Asp Val Trp Gly Gln Gly Thr Thr Val Thr Val Ser Ser
        115                 120                 125

<210> SEQ ID NO 7
<211> LENGTH: 120
<212> TYPE: PRT
<213> ORGANISM: Artificial Sequence
<220> FEATURE:
<223> OTHER INFORMATION: H2 heavy chain variable domain sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Lys Trp Tyr Tyr Gly Met Asp Val Trp Gly Arg
            100                 105                 110

Gly Thr Leu Val Thr Val Ser Ser
        115                 120

<210> SEQ ID NO 8
<211> LENGTH: 117
<212> TYPE: PRT
<213> ORGANISM: Artificial Sequence
<220> FEATURE:
<223> OTHER INFORMATION: H5 heavy chain variable domain sequence

<400> SEQUENCE: 8

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Ala Met Ser Trp Val Arg Gln Ala Pro Gly Lys Gly Leu Glu Trp Val
            35                  40                  45
Ser Ala Ile Ser Gly Ser Gly Gly Ser Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Arg Phe Arg Ala Ala Tyr Trp Gly Gln Gly Thr Leu
                100                 105                 110
Val Thr Val Ser Ser
            115
```

<210> SEQ ID NO 9
<211> LENGTH: 108
<212> TYPE: PRT
<213> ORGANISM: Artificial Sequence
<220> FEATURE:
<223> OTHER INFORMATION: A12 light chain variable domain sequence

<400> SEQUENCE: 9

```
Gln Ser Ala Leu Thr Gln Asp Pro Ala Val Ser Val Ala Leu Gly Gln
 1               5                  10                  15
Thr Val Arg Ile Thr Cys Arg Gly Asp Ser Leu Arg Asn Tyr Tyr Ala
            20                  25                  30
Ser Trp Tyr Gln Gln Lys Pro Gly Gln Ala Pro Val Leu Val Ile Tyr
         35                  40                  45
Gly Lys Asn Asn Arg Pro Ser Gly Ile Pro Asp Arg Phe Ser Gly Ser
 50                  55                  60
Phe Ser Gly Asn Thr Ala Ser Leu Thr Ile Thr Gly Ala Gln Ala Glu
 65                  70                  75                  80
Asp Glu Ala Asp Tyr Tyr Cys Asn Ser Arg Asp Ser Ser Ala Asn Gln
                 85                  90                  95
Met Phe Gly Gly Gly Thr Lys Val Thr Val Leu Gly
                100                 105
```

<210> SEQ ID NO 10
<211> LENGTH: 108
<212> TYPE: PRT
<213> ORGANISM: Artificial Sequence
<220> FEATURE:
<223> OTHER INFORMATION: C2 light chain variable domain sequence

<400> SEQUENCE: 10

```
Asp Ile Val Met Thr Gln Ser Pro Ser Ser Leu Ser Ala Ser Ile Gly
 1               5                  10                  15
Asp Arg Val Thr Ile Thr Cys Arg Ala Ser His Ser Ile Ser Ser Tyr
            20                  25                  30
Val Asn Trp Tyr Gln Lys Lys Pro Gly Lys Ala Pro Asn Leu Leu Ile
         35                  40                  45
Tyr Ala Ala Ser Tyr Leu Pro Arg Gly Val Pro Ser Arg Phe Ser Gly
 50                  55                  60
Ser Gly Leu Gly Thr Asp Phe Thr Leu Thr Ile Ser Asn Leu Gln Pro
 65                  70                  75                  80
Glu Asp Phe Ala Thr Tyr Tyr Cys Gln Glu Ser Tyr Ser Thr Pro Tyr
                 85                  90                  95
Ser Phe Gly Gln Gly Thr Lys Val Asp Ile Lys Arg
                100                 105
```

```
<210> SEQ ID NO 11
<211> LENGTH: 108
<212> TYPE: PRT
<213> ORGANISM: Artificial Sequence
<220> FEATURE:
<223> OTHER INFORMATION: E9 light chain variable domain sequence

<400> SEQUENCE: 11

Glu Ile Val Leu Thr Gln Ser Pro Ser Thr Leu Ser Ala Ser Ile Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Arg Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Leu Ile Ser Tyr Pro Leu
                85                  90                  95

Thr Phe Gly Gly Gly Thr Lys Val Glu Ile Lys Arg
            100                 105

<210> SEQ ID NO 12
<211> LENGTH: 110
<212> TYPE: PRT
<213> ORGANISM: Artificial Sequence
<220> FEATURE:
<223> OTHER INFORMATION: F1 light chain variable domain sequence

<400> SEQUENCE: 12

Ser Ala Leu Thr Gln Pro Ala Ser Val Ser Gly Ser Pro Gly Gln Ser
1               5                   10                  15

Ile Thr Ile Ser Cys Thr Gly Thr Ser Gly Asp Val Gly Gly Tyr Asn
            20                  25                  30

Tyr Val Ser Trp Tyr Gln Gln His Pro Gly Lys Ala Pro Lys Leu Met
        35                  40                  45

Ile Tyr Asp Val Ser Asn Arg Pro Ser Gly Val Ser Asn Arg Phe Ser
    50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Thr Ser Tyr Ala Gly Ser Arg
                85                  90                  95

Asn Leu Val Phe Gly Gly Gly Thr Lys Leu Thr Val Leu Gly
            100                 105                 110

<210> SEQ ID NO 13
<211> LENGTH: 111
<212> TYPE: PRT
<213> ORGANISM: Artificial Sequence
<220> FEATURE:
<223> OTHER INFORMATION: F11 light chain variable domain sequence

<400> SEQUENCE: 13

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45
```

-continued

Met Ile Tyr Asp Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Leu Phe Gly Gly Gly Thr Lys Leu Thr Val Leu Gly
            100                 105                 110

<210> SEQ ID NO 14
<211> LENGTH: 111
<212> TYPE: PRT
<213> ORGANISM: Artificial Sequence
<220> FEATURE:
<223> OTHER INFORMATION: G1 light chain variable domain sequence

<400> SEQUENCE: 14

Gln Ser Val Leu Thr Gln Pro Pro Ser Ala Ser Gly Thr Pro Gly Gln
1               5                   10                  15

Arg Val Thr Leu Phe Cys Ser Gly Ser Ser Asn Ile Ala Ser Asn
            20                  25                  30

Ser Val Lys Trp Tyr Gln Gln Pro Pro Gln Arg Ala Pro Lys Leu Leu
        35                  40                  45

Met Phe Ser Asp Asp Gln Arg Pro Ser Gly Val Pro Val Arg Phe Ser
    50                  55                  60

Ala Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Ala Glu Val Phe Gly Gly Gly Thr Lys Val Thr Val Leu Gly
            100                 105                 110

<210> SEQ ID NO 15
<211> LENGTH: 108
<212> TYPE: PRT
<213> ORGANISM: Artificial Sequence
<220> FEATURE:
<223> OTHER INFORMATION: H2 light chain variable domain sequence

<400> SEQUENCE: 15

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Thr
            20                  25                  30

Asn Trp Phe Gln Gln Lys Pro Gly Gln Ala Pro Leu Leu Val Val Tyr
        35                  40                  45

Ala Lys Asn Lys Arg Pro Ser Gly Ile Pro Asp Arg Phe Ser Gly Ser
    50                  55                  60

Gly Ser Gly Asp Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Tyr
                85                  90                  95

Leu Phe Ala Ala Gly Thr Lys Leu Thr Val Leu Gly
            100                 105

<210> SEQ ID NO 16
<211> LENGTH: 112
<212> TYPE: PRT
<213> ORGANISM: Artificial Sequence
<220> FEATURE:
<223> OTHER INFORMATION: H5 light chain variable domain sequence

<400> SEQUENCE: 16

Gln Ser Val Leu Thr Gln Pro Pro Ser Val Ser Ala Ala Pro Gly Gln
1               5                   10                  15

Lys Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Ser Glu Asp Glu Ala Asp Tyr Tyr Cys Ala Ala Trp Asp Asp Ile
                85                  90                  95

Leu Asn Gly Glu Ile Phe Gly Gly Gly Thr Lys Val Thr Val Leu Gly
            100                 105                 110

<210> SEQ ID NO 17
<211> LENGTH: 260
<212> TYPE: PRT
<213> ORGANISM: Artificial Sequence
<220> FEATURE:
<223> OTHER INFORMATION: A12 cys-diabody sequence

<400> SEQUENCE: 17

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ser Trp Tyr Arg Ser Tyr Tyr Phe Asp Tyr Trp
            100                 105                 110

Gly Gln Gly Thr Leu Val Thr Val Ser Ser Gly Gly Gly Gly Ser
            115                 120                 125

Gln Ser Ala Leu Thr Gln Asp Pro Ala Val Ser Val Ala Leu Gly Gln
            130                 135                 140

Thr Val Arg Ile Thr Cys Arg Gly Asp Ser Leu Arg Asn Tyr Tyr Ala
145                 150                 155                 160

Ser Trp Tyr Gln Gln Lys Pro Gly Gln Ala Pro Val Leu Val Ile Tyr
                165                 170                 175

Gly Lys Asn Asn Arg Pro Ser Gly Ile Pro Asp Arg Phe Ser Gly Ser
            180                 185                 190

Phe Ser Gly Asn Thr Ala Ser Leu Thr Ile Thr Gly Ala Gln Ala Glu
            195                 200                 205

Asp Glu Ala Asp Tyr Tyr Cys Asn Ser Arg Asp Ser Ser Ala Asn Gln
            210                 215                 220

```
Met Phe Gly Gly Gly Thr Lys Val Thr Val Leu Ala Ala Ala Glu
225                 230                 235                 240

Gln Lys Leu Ile Ser Glu Glu Asp Leu Asn Gly Ala Ala His His His
                245                 250                 255

His His His Cys
            260

<210> SEQ ID NO 18
<211> LENGTH: 259
<212> TYPE: PRT
<213> ORGANISM: Artificial Sequence
<220> FEATURE:
<223> OTHER INFORMATION: C2 cys-diabody sequence

<400> SEQUENCE: 18

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gln His Val Gly Glu Ser Arg Tyr Phe Asp Tyr Trp Gly
            100                 105                 110

Gln Gly Thr Leu Val Thr Val Ser Ser Gly Gly Gly Gly Ser Asp
        115                 120                 125

Ile Val Met Thr Gln Ser Pro Ser Ser Leu Ser Ala Ser Ile Gly Asp
    130                 135                 140

Arg Val Thr Ile Thr Cys Arg Ala Ser His Ser Ile Ser Ser Tyr Val
145                 150                 155                 160

Asn Trp Tyr Gln Lys Lys Pro Gly Lys Ala Pro Asn Leu Leu Ile Tyr
                165                 170                 175

Ala Ala Ser Tyr Leu Pro Arg Gly Val Pro Ser Arg Phe Ser Gly Ser
            180                 185                 190

Gly Leu Gly Thr Asp Phe Thr Leu Thr Ile Ser Asn Leu Gln Pro Glu
        195                 200                 205

Asp Phe Ala Thr Tyr Tyr Cys Gln Glu Ser Tyr Ser Thr Pro Tyr Ser
    210                 215                 220

Phe Gly Gln Gly Thr Lys Val Asp Ile Lys Arg Ala Ala Ala Glu Gln
225                 230                 235                 240

Lys Leu Ile Ser Glu Glu Asp Leu Asn Gly Ala Ala His His His His
                245                 250                 255

His His Cys

<210> SEQ ID NO 19
<211> LENGTH: 255
<212> TYPE: PRT
<213> ORGANISM: Artificial Sequence
<220> FEATURE:
<223> OTHER INFORMATION: E9 cys-diabody sequence
```

-continued

```
<400> SEQUENCE: 19

Gln Val Gln Leu Gln Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Gly Ser Ser Gly Gly Ser Thr His Asp Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ala Arg Gly Phe Asp Tyr Trp Gly Gln Gly Thr Leu
                100                 105                 110

Val Thr Val Ser Ser Gly Gly Gly Gly Ser Glu Ile Val Leu Thr
            115                 120                 125

Gln Ser Pro Ser Thr Leu Ser Ala Ser Ile Gly Asp Arg Val Thr Ile
    130                 135                 140

Thr Cys Arg Ala Ser Gln Gly Ile Ser Ser Tyr Leu Ala Trp Tyr Gln
145                 150                 155                 160

Gln Lys Pro Gly Lys Ala Pro Lys Leu Leu Ile Tyr Gly Ala Ser Ser
                165                 170                 175

Leu Gln Ser Gly Val Pro Ser Arg Phe Ser Gly Arg Gly Ser Gly Ala
            180                 185                 190

Asp Phe Thr Leu Thr Ile Ser Ser Leu Gln Pro Glu Asp Phe Ala Thr
        195                 200                 205

Tyr Tyr Cys Gln Gln Leu Ile Ser Tyr Pro Leu Thr Phe Gly Gly Gly
    210                 215                 220

Thr Lys Val Glu Ile Lys Arg Ala Ala Ala Glu Gln Lys Leu Ile Ser
225                 230                 235                 240

Glu Glu Asp Leu Asn Gly Ala Ala His His His His His Cys
                245                 250                 255

<210> SEQ ID NO 20
<211> LENGTH: 255
<212> TYPE: PRT
<213> ORGANISM: Artificial Sequence
<220> FEATURE:
<223> OTHER INFORMATION: F1 cys-diabody sequence

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Glu Gly Leu Glu Trp Met
        35                  40                  45

Gly Trp Met Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Ala Arg Ser His Tyr Trp Asp Ser Trp Ser Pro Gly Thr Leu Val Thr
            100                 105                 110

Val Ser Ser Gly Gly Gly Gly Ser Ser Ala Leu Thr Gln Pro Ala
        115                 120                 125

Ser Val Ser Gly Ser Pro Gly Gln Ser Ile Thr Ile Ser Cys Thr Gly
    130                 135                 140

Thr Ser Gly Asp Val Gly Gly Tyr Asn Tyr Val Ser Trp Tyr Gln Gln
145                 150                 155                 160

His Pro Gly Lys Ala Pro Lys Leu Met Ile Tyr Asp Val Ser Asn Arg
                165                 170                 175

Pro Ser Gly Val Ser Asn Arg Phe Ser Gly Ser Lys Ser Gly Asn Thr
            180                 185                 190

Ala Ser Leu Thr Ile Ser Gly Leu Gln Ala Glu Asp Glu Ala Asp Tyr
        195                 200                 205

Tyr Cys Thr Ser Tyr Ala Gly Ser Arg Asn Leu Val Phe Gly Gly Gly
    210                 215                 220

Thr Lys Leu Thr Val Leu Gly Ala Ala Ala Glu Gln Lys Leu Ile Ser
225                 230                 235                 240

Glu Glu Asp Leu Asn Gly Ala Ala His His His His His His Cys
                245                 250                 255
```

<210> SEQ ID NO 21
<211> LENGTH: 257
<212> TYPE: PRT
<213> ORGANISM: Artificial Sequence
<220> FEATURE:
<223> OTHER INFORMATION: F11 cys-diabody sequence

<400> SEQUENCE: 21

```
Gln Val Gln Leu Gln Glu Ser Gly Gly Gly Leu Leu Gln Pro Gly Gly
1               5                   10                  15

Ser Leu Arg Leu Ser Cys Ala Ala Ser Arg Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Asn Leu Tyr Gly Asp Tyr Asp Tyr Trp Gly Gln Gly Thr Leu Val
            100                 105                 110

Thr Val Ser Ser Gly Gly Gly Gly Ser Gln Ser Val Leu Thr Gln
        115                 120                 125

Pro Ala Ser Val Ser Gly Ser Pro Gly Gln Ser Ile Thr Ile Ser Cys
    130                 135                 140

Thr Gly Thr Ser Ser Asp Val Gly Gly Tyr Asn Tyr Val Ser Trp Tyr
145                 150                 155                 160

Gln Gln His Pro Gly Lys Ala Pro Lys Leu Met Ile Tyr Asp Val Ser
                165                 170                 175

Asn Arg Pro Ser Gly Val Ser Asn Arg Phe Ser Gly Ser Lys Ser Gly
            180                 185                 190

Asn Thr Ala Ser Leu Thr Ile Ser Gly Leu Gln Ala Glu Asp Glu Ala
        195                 200                 205
```

```
Asp Tyr Tyr Cys Ser Ser Tyr Thr Ser Ser Thr Leu Leu Phe Gly
        210                 215                 220

Gly Gly Thr Lys Leu Thr Val Leu Gly Ala Ala Glu Gln Lys Leu
225                 230                 235                 240

Ile Ser Glu Glu Asp Leu Asn Gly Ala Ala His His His His His
                245                 250                 255

Cys
```

```
<210> SEQ ID NO 22
<211> LENGTH: 269
<212> TYPE: PRT
<213> ORGANISM: Artificial Sequence
<220> FEATURE:
<223> OTHER INFORMATION: G1 cys-diabody sequence

<400> SEQUENCE: 22

Gln Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Ser Asp Tyr Gly Asp Tyr Asp Tyr Tyr
            100                 105                 110

Tyr Gly Met Asp Val Trp Gly Gln Gly Thr Thr Val Thr Val Ser Ser
        115                 120                 125

Gly Gly Gly Gly Ser Gln Ser Val Leu Thr Gln Pro Pro Ser Ala
    130                 135                 140

Ser Gly Thr Pro Gly Gln Arg Val Thr Leu Phe Cys Ser Gly Ser Ser
145                 150                 155                 160

Ser Asn Ile Ala Ser Asn Ser Val Lys Trp Tyr Gln Gln Pro Pro Gln
                165                 170                 175

Arg Ala Pro Lys Leu Leu Met Phe Ser Asp Asp Gln Arg Pro Ser Gly
            180                 185                 190

Val Pro Val Arg Phe Ser Ala Ser Lys Ser Gly Thr Ser Ala Ser Leu
        195                 200                 205

Ala Ile Ser Gly Leu Gln Ser Glu Asp Glu Ala Asp Tyr Tyr Cys Ala
    210                 215                 220

Ala Trp Asp Asp Ser Leu Asn Ala Glu Val Phe Gly Gly Thr Lys
225                 230                 235                 240

Val Thr Val Leu Gly Ala Ala Ala Glu Gln Lys Leu Ile Ser Glu Glu
                245                 250                 255

Asp Leu Asn Gly Ala Ala His His His His His Cys
            260                 265
```

```
<210> SEQ ID NO 23
<211> LENGTH: 258
<212> TYPE: PRT
<213> ORGANISM: Artificial Sequence
<220> FEATURE:
<223> OTHER INFORMATION: H2 cys-diabody sequence
```

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Lys Trp Tyr Tyr Gly Met Asp Val Trp Gly Arg
            100                 105                 110

Gly Thr Leu Val Thr Val Ser Ser Gly Gly Gly Gly Ser Ser Ser
        115                 120                 125

Glu Leu Thr Gln Asp Pro Ala Val Ser Val Ala Leu Gly Gln Thr Val
    130                 135                 140

Arg Ile Thr Cys Gln Gly Asp Ser Leu Arg Ser Tyr Tyr Thr Asn Trp
145                 150                 155                 160

Phe Gln Gln Lys Pro Gly Gln Ala Pro Leu Leu Val Val Tyr Ala Lys
                165                 170                 175

Asn Lys Arg Pro Ser Gly Ile Pro Asp Arg Phe Ser Gly Ser Gly Ser
            180                 185                 190

Gly Asp Thr Ala Ser Leu Thr Ile Thr Gly Ala Gln Ala Glu Asp Glu
        195                 200                 205

Ala Asp Tyr Tyr Cys Asn Ser Arg Asp Ser Ser Gly Asn Tyr Leu Phe
    210                 215                 220

Ala Ala Gly Thr Lys Leu Thr Val Leu Gly Ala Ala Ala Glu Gln Lys
225                 230                 235                 240

Leu Ile Ser Glu Glu Asp Leu Asn Gly Ala Ala His His His His His
                245                 250                 255

His Cys

<210> SEQ ID NO 24
<211> LENGTH: 259
<212> TYPE: PRT
<213> ORGANISM: Artificial Sequence
<220> FEATURE:
<223> OTHER INFORMATION: H5 cys-diabody sequence

<400> SEQUENCE: 24

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Phe Arg Ala Ala Tyr Trp Gly Gln Gly Thr Leu
            100                 105                 110

Val Thr Val Ser Ser Gly Gly Gly Gly Ser Gln Ser Val Leu Thr
        115                 120                 125

Gln Pro Pro Ser Val Ser Ala Ala Pro Gly Gln Lys Val Thr Ile Ser
    130                 135                 140

Cys Thr Gly Ser Ser Ser Asn Ile Gly Ala Gly Tyr Asp Val His Trp
145                 150                 155                 160

Tyr Gln Gln Leu Pro Gly Thr Ala Pro Lys Leu Leu Ile Tyr Gly Asn
                165                 170                 175

Ser Asn Arg Pro Ser Gly Val Pro Asp Arg Phe Ser Gly Ser Lys Ser
            180                 185                 190

Gly Thr Ser Ala Ser Leu Ala Ile Ser Gly Leu Gln Ser Glu Asp Glu
        195                 200                 205

Ala Asp Tyr Tyr Cys Ala Ala Trp Asp Asp Ile Leu Asn Gly Glu Ile
    210                 215                 220

Phe Gly Gly Gly Thr Lys Val Thr Val Leu Gly Ala Ala Ala Glu Gln
225                 230                 235                 240

Lys Leu Ile Ser Glu Glu Asp Leu Asn Gly Ala Ala His His His His
                245                 250                 255

His His Cys

<210> SEQ ID NO 25
<211> LENGTH: 246
<212> TYPE: PRT
<213> ORGANISM: Artificial Sequence
<220> FEATURE:
<223> OTHER INFORMATION: synthetic A12 ScFv sequence

<400> SEQUENCE: 25

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ser Ser Trp Tyr Arg Ser Tyr Tyr Phe Asp Tyr Trp
            100                 105                 110

Gly Gln Gly Thr Leu Val Thr Val Ser Ser Gly Gly Gly Gly Gly Ser
        115                 120                 125

Gly Gly Gly Gly Ser Gly Gly Gly Ser Gln Ser Ala Leu Thr Gln
    130                 135                 140

Asp Pro Ala Val Ser Val Ala Leu Gly Gln Thr Val Arg Ile Thr Cys
145                 150                 155                 160

Arg Gly Asp Ser Leu Arg Asn Tyr Tyr Ala Ser Trp Tyr Gln Gln Lys
                165                 170                 175

Pro Gly Gln Ala Pro Val Leu Val Ile Tyr Gly Lys Asn Asn Arg Pro
            180                 185                 190

Ser Gly Ile Pro Asp Arg Phe Ser Gly Ser Phe Ser Gly Asn Thr Ala
            195                 200                 205

Ser Leu Thr Ile Thr Gly Ala Gln Ala Glu Asp Glu Ala Asp Tyr Tyr
    210                 215                 220

Cys Asn Ser Arg Asp Ser Ser Ala Asn Gln Met Phe Gly Gly Gly Thr
225                 230                 235                 240

Lys Val Thr Val Leu Gly
                245

<210> SEQ ID NO 26
<211> LENGTH: 245
<212> TYPE: PRT
<213> ORGANISM: Artificial Sequence
<220> FEATURE:
<223> OTHER INFORMATION: synthetic C2 ScFv sequence

<400> SEQUENCE: 26

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gln His Val Gly Glu Gln Ser Arg Tyr Phe Asp Tyr Trp Gly
            100                 105                 110

Gln Gly Thr Leu Val Thr Val Ser Ser Gly Gly Gly Gly Ser Gly
        115                 120                 125

Gly Gly Ser Gly Gly Gly Ser Asp Ile Val Met Thr Gln Ser
    130                 135                 140

Pro Ser Ser Leu Ser Ala Ser Ile Gly Asp Arg Val Thr Ile Thr Cys
145                 150                 155                 160

Arg Ala Ser His Ser Ile Ser Ser Tyr Val Asn Trp Tyr Gln Lys Lys
                165                 170                 175

Pro Gly Lys Ala Pro Asn Leu Leu Ile Tyr Ala Ala Ser Tyr Leu Pro
            180                 185                 190

Arg Gly Val Pro Ser Arg Phe Ser Gly Ser Gly Leu Gly Thr Asp Phe
        195                 200                 205

Thr Leu Thr Ile Ser Asn Leu Gln Pro Glu Asp Phe Ala Thr Tyr Tyr
    210                 215                 220

Cys Gln Glu Ser Tyr Ser Thr Pro Tyr Ser Phe Gly Gln Gly Thr Lys
225                 230                 235                 240

Val Asp Ile Lys Arg
                245

<210> SEQ ID NO 27
<211> LENGTH: 241
<212> TYPE: PRT
<213> ORGANISM: Artificial Sequence
<220> FEATURE:
<223> OTHER INFORMATION: synthetic E9 ScFv sequence

<400> SEQUENCE: 27

```
Gln Val Gln Leu Gln Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ser Ala Ile Gly Ser Ser Gly Gly Ser Thr His Asp Ala Asp Thr Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Asp Arg Ala Arg Gly Phe Asp Tyr Trp Gly Gln Gly Thr Leu
            100                 105                 110
Val Thr Val Ser Ser Gly Gly Gly Gly Ser Gly Gly Gly Gly Ser
        115                 120                 125
Gly Gly Gly Gly Ser Glu Ile Val Leu Thr Gln Ser Pro Ser Thr Leu
    130                 135                 140
Ser Ala Ser Ile Gly Asp Arg Val Thr Ile Thr Cys Arg Ala Ser Gln
145                 150                 155                 160
Gly Ile Ser Ser Tyr Leu Ala Trp Tyr Gln Gln Lys Pro Gly Lys Ala
                165                 170                 175
Pro Lys Leu Leu Ile Tyr Gly Ala Ser Ser Leu Gln Ser Gly Val Pro
            180                 185                 190
Ser Arg Phe Ser Gly Arg Gly Ser Gly Ala Asp Phe Thr Leu Thr Ile
        195                 200                 205
Ser Ser Leu Gln Pro Glu Asp Phe Ala Thr Tyr Tyr Cys Gln Gln Leu
    210                 215                 220
Ile Ser Tyr Pro Leu Thr Phe Gly Gly Gly Thr Lys Val Glu Ile Lys
225                 230                 235                 240
Arg
```

<210> SEQ ID NO 28
<211> LENGTH: 241
<212> TYPE: PRT
<213> ORGANISM: Artificial Sequence
<220> FEATURE:
<223> OTHER INFORMATION: synthetic F1 ScFv sequence

<400> SEQUENCE: 28

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Tyr Met His Trp Val Arg Gln Ala Pro Gly Glu Gly Leu Glu Trp Met
        35                  40                  45
Gly Trp Met Asn Pro Asn Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Ser His Tyr Trp Asp Ser Trp Ser Pro Gly Thr Leu Val Thr
            100                 105                 110
```

Val Ser Ser Gly Gly Gly Gly Ser Gly Gly Gly Ser Gly Gly
        115                 120                 125

Gly Gly Ser Ser Ala Leu Thr Gln Pro Ala Ser Val Ser Gly Ser Pro
130                 135                 140

Gly Gln Ser Ile Thr Ile Ser Cys Thr Gly Thr Ser Gly Asp Val Gly
145                 150                 155                 160

Gly Tyr Asn Tyr Val Ser Trp Tyr Gln Gln His Pro Gly Lys Ala Pro
                165                 170                 175

Lys Leu Met Ile Tyr Asp Val Ser Asn Arg Pro Ser Gly Val Ser Asn
            180                 185                 190

Arg Phe Ser Gly Ser Lys Ser Gly Asn Thr Ala Ser Leu Thr Ile Ser
        195                 200                 205

Gly Leu Gln Ala Glu Asp Glu Ala Asp Tyr Tyr Cys Thr Ser Tyr Ala
    210                 215                 220

Gly Ser Arg Asn Leu Val Phe Gly Gly Gly Thr Lys Leu Thr Val Leu
225                 230                 235                 240

Gly

<210> SEQ ID NO 29
<211> LENGTH: 243
<212> TYPE: PRT
<213> ORGANISM: Artificial Sequence
<220> FEATURE:
<223> OTHER INFORMATION: synthetic F11 ScFv sequence

<400> SEQUENCE: 29

Gln Val Gln Leu Gln Glu Ser Gly Gly Gly Leu Leu Gln Pro Gly Gly
1               5                   10                  15

Ser Leu Arg Leu Ser Cys Ala Ala Ser Arg Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Asn Leu Tyr Gly Asp Tyr Asp Tyr Trp Gly Gln Gly Thr Leu Val
            100                 105                 110

Thr Val Ser Ser Gly Gly Gly Gly Ser Gly Gly Gly Gly Ser Gly
        115                 120                 125

Gly Gly Gly Ser Gln Ser Val Leu Thr Gln Pro Ala Ser Val Ser Gly
    130                 135                 140

Ser Pro Gly Gln Ser Ile Thr Ile Ser Cys Thr Gly Thr Ser Ser Asp
145                 150                 155                 160

Val Gly Gly Tyr Asn Tyr Val Ser Trp Tyr Gln Gln His Pro Gly Lys
                165                 170                 175

Ala Pro Lys Leu Met Ile Tyr Asp Val Ser Asn Arg Pro Ser Gly Val
            180                 185                 190

Ser Asn Arg Phe Ser Gly Ser Lys Ser Gly Asn Thr Ala Ser Leu Thr
        195                 200                 205

Ile Ser Gly Leu Gln Ala Glu Asp Glu Ala Asp Tyr Tyr Cys Ser Ser
    210                 215                 220

```
Tyr Thr Ser Ser Ser Thr Leu Leu Phe Gly Gly Gly Thr Lys Leu Thr
225                 230                 235                 240

Val Leu Gly
```

<210> SEQ ID NO 30
<211> LENGTH: 255
<212> TYPE: PRT
<213> ORGANISM: Artificial Sequence
<220> FEATURE:
<223> OTHER INFORMATION: synthetic G1 ScFv sequence

<400> SEQUENCE: 30

```
Gln Val Gln Leu Gln Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Ser Asp Asp Tyr Gly Asp Tyr Asp Tyr Tyr
            100                 105                 110

Tyr Gly Met Asp Val Trp Gly Gln Gly Thr Thr Val Thr Val Ser Ser
        115                 120                 125

Gly Gly Gly Gly Gly Ser Gly Gly Gly Ser Gly Gly Gly Gly Ser
    130                 135                 140

Gln Ser Val Leu Thr Gln Pro Pro Ser Ala Ser Gly Thr Pro Gly Gln
145                 150                 155                 160

Arg Val Thr Leu Phe Cys Ser Gly Ser Ser Ser Asn Ile Ala Ser Asn
                165                 170                 175

Ser Val Lys Trp Tyr Gln Gln Pro Pro Gln Arg Ala Pro Lys Leu Leu
            180                 185                 190

Met Phe Ser Asp Asp Gln Arg Pro Ser Gly Val Pro Val Arg Phe Ser
        195                 200                 205

Ala Ser Lys Ser Gly Thr Ser Ala Ser Leu Ala Ile Ser Gly Leu Gln
    210                 215                 220

Ser Glu Asp Glu Ala Asp Tyr Tyr Cys Ala Ala Trp Asp Asp Ser Leu
225                 230                 235                 240

Asn Ala Glu Val Phe Gly Gly Gly Thr Lys Val Thr Val Leu Gly
                245                 250                 255
```

<210> SEQ ID NO 31
<211> LENGTH: 244
<212> TYPE: PRT
<213> ORGANISM: Artificial Sequence
<220> FEATURE:
<223> OTHER INFORMATION: synthetic H2 ScFv sequence

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

```
Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Gly Lys Trp Tyr Tyr Gly Met Asp Val Trp Gly Arg
            100                 105                 110

Gly Thr Leu Val Thr Val Ser Gly Gly Gly Gly Ser Gly Gly
            115                 120                 125

Gly Gly Ser Gly Gly Gly Ser Ser Ser Glu Leu Thr Gln Asp Pro
        130                 135                 140

Ala Val Ser Val Ala Leu Gly Gln Thr Val Arg Ile Thr Cys Gln Gly
145                 150                 155                 160

Asp Ser Leu Arg Ser Tyr Tyr Thr Asn Trp Phe Gln Gln Lys Pro Gly
                165                 170                 175

Gln Ala Pro Leu Leu Val Val Tyr Ala Lys Asn Lys Arg Pro Ser Gly
            180                 185                 190

Ile Pro Asp Arg Phe Ser Gly Ser Gly Ser Gly Asp Thr Ala Ser Leu
            195                 200                 205

Thr Ile Thr Gly Ala Gln Ala Glu Asp Glu Ala Asp Tyr Tyr Cys Asn
            210                 215                 220

Ser Arg Asp Ser Ser Gly Asn Tyr Leu Phe Ala Ala Gly Thr Lys Leu
225                 230                 235                 240

Thr Val Leu Gly

<210> SEQ ID NO 32
<211> LENGTH: 245
<212> TYPE: PRT
<213> ORGANISM: Artificial Sequence
<220> FEATURE:
<223> OTHER INFORMATION: synthetic H5 ScFv sequence

<400> SEQUENCE: 32

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Phe Arg Ala Ala Ala Tyr Trp Gly Gln Gly Thr Leu
            100                 105                 110

Val Thr Val Ser Ser Gly Gly Gly Gly Ser Gly Gly Gly Gly Ser
            115                 120                 125

Gly Gly Gly Gly Ser Gln Ser Val Leu Thr Gln Pro Pro Ser Val Ser
        130                 135                 140
```

-continued

```
Ala Ala Pro Gly Gln Lys Val Thr Ile Ser Cys Thr Gly Ser Ser Ser
145                 150                 155                 160

Asn Ile Gly Ala Gly Tyr Asp Val His Trp Tyr Gln Gln Leu Pro Gly
                165                 170                 175

Thr Ala Pro Lys Leu Leu Ile Tyr Gly Asn Ser Asn Arg Pro Ser Gly
            180                 185                 190

Val Pro Asp Arg Phe Ser Gly Ser Lys Ser Gly Thr Ser Ala Ser Leu
        195                 200                 205

Ala Ile Ser Gly Leu Gln Ser Glu Asp Glu Ala Asp Tyr Tyr Cys Ala
    210                 215                 220

Ala Trp Asp Asp Ile Leu Asn Gly Glu Ile Phe Gly Gly Gly Thr Lys
225                 230                 235                 240

Val Thr Val Leu Gly
                245

<210> SEQ ID NO 33
<211> LENGTH: 10
<212> TYPE: PRT
<213> ORGANISM: Artificial Sequence
<220> FEATURE:
<223> OTHER INFORMATION: synthetic A12 CDR-H1

<400> SEQUENCE: 33

Gly Phe Thr Phe Ser Ser Tyr Ala Met Ser
1               5                   10

<210> SEQ ID NO 34
<211> LENGTH: 17
<212> TYPE: PRT
<213> ORGANISM: Artificial Sequence
<220> FEATURE:
<223> OTHER INFORMATION: synthetic A12 CDR-H2

<400> SEQUENCE: 34

Ala Ile Ser Gly Ser Gly Gly Ser Thr Tyr Tyr Ala Asp Ser Val Lys
1               5                   10                  15

Gly

<210> SEQ ID NO 35
<211> LENGTH: 13
<212> TYPE: PRT
<213> ORGANISM: Artificial Sequence
<220> FEATURE:
<223> OTHER INFORMATION: synthetic A12 CDR-H3

<400> SEQUENCE: 35

Ser Ser Ser Ser Trp Tyr Arg Ser Tyr Tyr Phe Asp Tyr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: synthetic C2 CDR-H1

<400> SEQUENCE: 36

Gly Phe Thr Phe Ser Ser Tyr Ala Met Ser
1               5                   10
```

```
<210> SEQ ID NO 37
<211> LENGTH: 17
<212> TYPE: PRT
<213> ORGANISM: Artificial Sequence
<220> FEATURE:
<223> OTHER INFORMATION: synthetic C2 CDR-H2

<400> SEQUENCE: 37

Ala Ile Ser Gly Ser Gly Gly Ser Thr Tyr Tyr Ala Asp Ser Val Lys
1               5                   10                  15

Gly

<210> SEQ ID NO 38
<211> LENGTH: 12
<212> TYPE: PRT
<213> ORGANISM: Artificial Sequence
<220> FEATURE:
<223> OTHER INFORMATION: synthetic C2 CDR-H3

<400> SEQUENCE: 38

Gln His Val Gly Glu Gln Ser Arg Tyr Phe Asp Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: synthetic E9 CDR-H1

<400> SEQUENCE: 39

Gly Phe Thr Phe Ser Ser Tyr Gly Met His
1               5                   10

<210> SEQ ID NO 40
<211> LENGTH: 17
<212> TYPE: PRT
<213> ORGANISM: Artificial Sequence
<220> FEATURE:
<223> OTHER INFORMATION: synthetic E9 CDR-H2

<400> SEQUENCE: 40

Ala Ile Gly Ser Ser Gly Gly Ser Thr His Asp Ala Asp Thr Val Lys
1               5                   10                  15

Gly

<210> SEQ ID NO 41
<211> LENGTH: 8
<212> TYPE: PRT
<213> ORGANISM: Artificial Sequence
<220> FEATURE:
<223> OTHER INFORMATION: synthetic E9 CDR-H3

<400> SEQUENCE: 41

Asp Arg Ala Arg Gly Phe Asp Tyr
1               5

<210> SEQ ID NO 42
<211> LENGTH: 10
<212> TYPE: PRT
<213> ORGANISM: Artificial Sequence
<220> FEATURE:
<223> OTHER INFORMATION: synthetic F1 CDR-H1
```

```
<400> SEQUENCE: 42

Gly Tyr Thr Phe Thr Asp Tyr Tyr Met His
1               5                   10

<210> SEQ ID NO 43
<211> LENGTH: 17
<212> TYPE: PRT
<213> ORGANISM: Artificial Sequence
<220> FEATURE:
<223> OTHER INFORMATION: synthetic F1 CDR-H2

<400> SEQUENCE: 43

Trp Met Asn Pro Asn Ser Gly Gly Thr Asn Tyr Ala Gln Lys Phe Gln
1               5                   10                  15

Gly

<210> SEQ ID NO 44
<211> LENGTH: 6
<212> TYPE: PRT
<213> ORGANISM: Artificial Sequence
<220> FEATURE:
<223> OTHER INFORMATION: synthetic F1 CDR-H3

<400> SEQUENCE: 44

Ser His Tyr Trp Asp Ser
1               5

<210> SEQ ID NO 45
<211> LENGTH: 10
<212> TYPE: PRT
<213> ORGANISM: Artificial Sequence
<220> FEATURE:
<223> OTHER INFORMATION: synthetic F11 CDR-H1

<400> SEQUENCE: 45

Arg Phe Thr Phe Ser Asn Tyr Ala Met Ser
1               5                   10

<210> SEQ ID NO 46
<211> LENGTH: 17
<212> TYPE: PRT
<213> ORGANISM: Artificial Sequence
<220> FEATURE:
<223> OTHER INFORMATION: synthetic F11 CDR-H2

<400> SEQUENCE: 46

Ala Ile Ser Gly Ser Gly Ala Ser Thr Tyr Tyr Ala Asp Ser Val Lys
1               5                   10                  15

Gly

<210> SEQ ID NO 47
<211> LENGTH: 7
<212> TYPE: PRT
<213> ORGANISM: Artificial Sequence
<220> FEATURE:
<223> OTHER INFORMATION: synthetic F11 CDR-H3

<400> SEQUENCE: 47

Leu Tyr Gly Asp Tyr Asp Tyr
1               5

<210> SEQ ID NO 48
<211> LENGTH: 10
<212> TYPE: PRT
<213> ORGANISM: Artificial Sequence
```

```
<220> FEATURE:
<223> OTHER INFORMATION: synthetic G1 CDR-H1

<400> SEQUENCE: 48

Gly Phe Thr Phe Ser Ser Tyr Ser Met Asn
1               5                   10

<210> SEQ ID NO 49
<211> LENGTH: 17
<212> TYPE: PRT
<213> ORGANISM: Artificial Sequence
<220> FEATURE:
<223> OTHER INFORMATION: synthetic G1 CDR-H2

<400> SEQUENCE: 49

Ser Ile Ser Ser Ser Ser Ser Tyr Ile Tyr Tyr Ala Asp Ser Val Lys
1               5                   10                  15
Gly

<210> SEQ ID NO 50
<211> LENGTH: 19
<212> TYPE: PRT
<213> ORGANISM: Artificial Sequence
<220> FEATURE:
<223> OTHER INFORMATION: synthetic G1 CDR-H3

<400> SEQUENCE: 50

Asp Leu Pro Ser Asp Asp Tyr Gly Asp Tyr Asp Tyr Tyr Tyr Gly
1               5                   10                  15
Met Asp Val

<210> SEQ ID NO 51
<211> LENGTH: 10
<212> TYPE: PRT
<213> ORGANISM: Artificial Sequence
<220> FEATURE:
<223> OTHER INFORMATION: synthetic H2 CDR-H1

<400> SEQUENCE: 51

Gly Phe Thr Phe Ser Thr Tyr Ala Met Ser
1               5                   10

<210> SEQ ID NO 52
<211> LENGTH: 17
<212> TYPE: PRT
<213> ORGANISM: Artificial Sequence
<220> FEATURE:
<223> OTHER INFORMATION: synthetic H2 CDR-H2

<400> SEQUENCE: 52

Ala Ile Ser Gly Ser Gly Gly Ser Thr Tyr Tyr Ala Asp Ser Val Lys
1               5                   10                  15
Gly

<210> SEQ ID NO 53
<211> LENGTH: 11
<212> TYPE: PRT
<213> ORGANISM: Artificial Sequence
<220> FEATURE:
<223> OTHER INFORMATION: synthetic H2 CDR-H3

<400> SEQUENCE: 53

Glu Gly Gly Lys Trp Tyr Tyr Gly Met Asp Val
1               5                   10
```

<210> SEQ ID NO 54
<211> LENGTH: 10
<212> TYPE: PRT
<213> ORGANISM: Artificial Sequence
<220> FEATURE:
<223> OTHER INFORMATION: synthetic H5 CDR-H1

<400> SEQUENCE: 54

Gly Phe Thr Phe Ser Asn Tyr Ala Met Ser
1 5 10

<210> SEQ ID NO 55
<211> LENGTH: 17
<212> TYPE: PRT
<213> ORGANISM: Artificial Sequence
<220> FEATURE:
<223> OTHER INFORMATION: synthetic H5 CDR-H2

<400> SEQUENCE: 55

Ala Ile Ser Gly Ser Gly Gly Ser Thr Tyr Tyr Ala Asp Ser Val Lys
1 5 10 15

Gly

<210> SEQ ID NO 56
<211> LENGTH: 8
<212> TYPE: PRT
<213> ORGANISM: Artificial Sequence
<220> FEATURE:
<223> OTHER INFORMATION: synthetic H5 CDR-H1

<400> SEQUENCE: 56

Asp Arg Phe Arg Ala Ala Ala Tyr
1 5

<210> SEQ ID NO 57
<211> LENGTH: 11
<212> TYPE: PRT
<213> ORGANISM: Artificial Sequence
<220> FEATURE:
<223> OTHER INFORMATION: synthetic A12 CDR-L1

<400> SEQUENCE: 57

Arg Gly Asp Ser Leu Arg Asn Tyr Tyr Ala Ser
1 5 10

<210> SEQ ID NO 58
<211> LENGTH: 7
<212> TYPE: PRT
<213> ORGANISM: Artificial Sequence
<220> FEATURE:
<223> OTHER INFORMATION: synthetic A12 CDR-L2

<400> SEQUENCE: 58

Gly Lys Asn Asn Arg Pro Ser
1 5

<210> SEQ ID NO 59
<211> LENGTH: 10
<212> TYPE: PRT
<213> ORGANISM: Artificial Sequence
<220> FEATURE:
<223> OTHER INFORMATION: synthetic A12 CDR-L3

<400> SEQUENCE: 59

Asn Ser Arg Asp Ser Ser Ala Asn Gln Met
1 5 10

```
<210> SEQ ID NO 60
<211> LENGTH: 11
<212> TYPE: PRT
<213> ORGANISM: Artificial Sequence
<220> FEATURE:
<223> OTHER INFORMATION: synthetic C2 CDR-L1

<400> SEQUENCE: 60

Arg Ala Ser His Ser Ile Ser Ser Tyr Val Asn
1               5                   10

<210> SEQ ID NO 61
<211> LENGTH: 7
<212> TYPE: PRT
<213> ORGANISM: Artificial Sequence
<220> FEATURE:
<223> OTHER INFORMATION: synthetic C2 CDR-L2

<400> SEQUENCE: 61

Ala Ala Ser Tyr Leu Pro Arg
1               5

<210> SEQ ID NO 62
<211> LENGTH: 9
<212> TYPE: PRT
<213> ORGANISM: Artificial Sequence
<220> FEATURE:
<223> OTHER INFORMATION: synthetic C2 CDR-L3

<400> SEQUENCE: 62

Gln Glu Ser Tyr Ser Thr Pro Tyr Ser
1               5

<210> SEQ ID NO 63
<211> LENGTH: 11
<212> TYPE: PRT
<213> ORGANISM: Artificial Sequence
<220> FEATURE:
<223> OTHER INFORMATION: synthetic E9 CDR-L1

<400> SEQUENCE: 63

Arg Ala Ser Gln Gly Ile Ser Ser Tyr Leu Ala
1               5                   10

<210> SEQ ID NO 64
<211> LENGTH: 7
<212> TYPE: PRT
<213> ORGANISM: Artificial Sequence
<220> FEATURE:
<223> OTHER INFORMATION: synthetic E9 CDR-L2

<400> SEQUENCE: 64

Gly Ala Ser Ser Leu Gln Ser
1               5

<210> SEQ ID NO 65
<211> LENGTH: 9
<212> TYPE: PRT
<213> ORGANISM: Artificial Sequence
<220> FEATURE:
<223> OTHER INFORMATION: synthetic E9 CDR-L3

<400> SEQUENCE: 65

Gln Gln Leu Ile Ser Tyr Pro Leu Thr
1               5
```

```
<210> SEQ ID NO 66
<211> LENGTH: 14
<212> TYPE: PRT
<213> ORGANISM: Artificial Sequence
<220> FEATURE:
<223> OTHER INFORMATION: synthetic F1 CDR-L1

<400> SEQUENCE: 66

Thr Gly Thr Ser Gly Asp Val Gly Gly Tyr Asn Tyr Val Ser
1               5                   10

<210> SEQ ID NO 67
<211> LENGTH: 7
<212> TYPE: PRT
<213> ORGANISM: Artificial Sequence
<220> FEATURE:
<223> OTHER INFORMATION: synthetic F1 CDR-L2

<400> SEQUENCE: 67

Asp Val Ser Asn Arg Pro Ser
1               5

<210> SEQ ID NO 68
<211> LENGTH: 10
<212> TYPE: PRT
<213> ORGANISM: Artificial Sequence
<220> FEATURE:
<223> OTHER INFORMATION: synthetic F1 CDR-L3

<400> SEQUENCE: 68

Thr Ser Tyr Ala Gly Ser Arg Asn Leu Val
1               5                   10

<210> SEQ ID NO 69
<211> LENGTH: 14
<212> TYPE: PRT
<213> ORGANISM: Artificial Sequence
<220> FEATURE:
<223> OTHER INFORMATION: synthetic F11 CDR-L1

<400> SEQUENCE: 69

Thr Gly Thr Ser Ser Asp Val Gly Gly Tyr Asn Tyr Val Ser
1               5                   10

<210> SEQ ID NO 70
<211> LENGTH: 7
<212> TYPE: PRT
<213> ORGANISM: Artificial Sequence
<220> FEATURE:
<223> OTHER INFORMATION: synthetic F11 CDR-L2

<400> SEQUENCE: 70

Asp Val Ser Asn Arg Pro Ser
1               5

<210> SEQ ID NO 71
<211> LENGTH: 10
<212> TYPE: PRT
<213> ORGANISM: Artificial Sequence
<220> FEATURE:
<223> OTHER INFORMATION: synthetic F11 CDR-L3

<400> SEQUENCE: 71

Ser Ser Tyr Thr Ser Ser Ser Thr Leu Leu
1               5                   10
```

<210> SEQ ID NO 72
<211> LENGTH: 13
<212> TYPE: PRT
<213> ORGANISM: Artificial Sequence
<220> FEATURE:
<223> OTHER INFORMATION: synthetic G1 CDR-L1

<400> SEQUENCE: 72

Ser Gly Ser Ser Ser Asn Ile Ala Ser Asn Ser Val Lys
1               5                   10

<210> SEQ ID NO 73
<211> LENGTH: 7
<212> TYPE: PRT
<213> ORGANISM: Artificial Sequence
<220> FEATURE:
<223> OTHER INFORMATION: synthetic G1 CDR-L2

<400> SEQUENCE: 73

Ser Asp Asp Gln Arg Pro Ser
1               5

<210> SEQ ID NO 74
<211> LENGTH: 11
<212> TYPE: PRT
<213> ORGANISM: Artificial Sequence
<220> FEATURE:
<223> OTHER INFORMATION: synthetic G1 CDR-L3

<400> SEQUENCE: 74

Ala Ala Trp Asp Asp Ser Leu Asn Ala Glu Val
1               5                   10

<210> SEQ ID NO 75
<211> LENGTH: 11
<212> TYPE: PRT
<213> ORGANISM: Artificial Sequence
<220> FEATURE:
<223> OTHER INFORMATION: synthetic H2 CDR-L1

<400> SEQUENCE: 75

Gln Gly Asp Ser Leu Arg Ser Tyr Tyr Thr Asn
1               5                   10

<210> SEQ ID NO 76
<211> LENGTH: 7
<212> TYPE: PRT
<213> ORGANISM: Artificial Sequence
<220> FEATURE:
<223> OTHER INFORMATION: synthetic H2 CDR-L2

<400> SEQUENCE: 76

Ala Lys Asn Lys Arg Pro Ser
1               5

<210> SEQ ID NO 77
<211> LENGTH: 10
<212> TYPE: PRT
<213> ORGANISM: Artificial Sequence
<220> FEATURE:
<223> OTHER INFORMATION: synthetic H2 CDR-L3

<400> SEQUENCE: 77

Asn Ser Arg Asp Ser Ser Gly Asn Tyr Leu
1               5                   10

<210> SEQ ID NO 78
<211> LENGTH: 14
<212> TYPE: PRT
<213> ORGANISM: Artificial Sequence
<220> FEATURE:
<223> OTHER INFORMATION: synthetic H5 CDR-L1

<400> SEQUENCE: 78

Thr Gly Ser Ser Ser Asn Ile Gly Ala Gly Tyr Asp Val His
1 5 10

<210> SEQ ID NO 79
<211> LENGTH: 7
<212> TYPE: PRT
<213> ORGANISM: Artificial Sequence
<220> FEATURE:
<223> OTHER INFORMATION: synthetic H5 CDR-L2

<400> SEQUENCE: 79

Gly Asn Ser Asn Arg Pro Ser
1 5

<210> SEQ ID NO 80
<211> LENGTH: 11
<212> TYPE: PRT
<213> ORGANISM: Artificial Sequence
<220> FEATURE:
<223> OTHER INFORMATION: synthetic H5 CDR-L3

<400> SEQUENCE: 80

Ala Ala Trp Asp Asp Ile Leu Asn Gly Glu Ile
1 5 10

<210> SEQ ID NO 81
<211> LENGTH: 24
<212> TYPE: PRT
<213> ORGANISM: Artificial Sequence
<220> FEATURE:
<223> OTHER INFORMATION: isolated synthetic linker

<400> SEQUENCE: 81

Ala Ala Ala Glu Gln Lys Leu Ile Ser Glu Glu Asp Leu Asn Gly Ala
1 5 10 15

Ala His His His His His His Cys
20

<210> SEQ ID NO 82
<211> LENGTH: 5
<212> TYPE: PRT
<213> ORGANISM: Artificial Sequence
<220> FEATURE:
<223> OTHER INFORMATION: isolated synthetic linker

<400> SEQUENCE: 82

Gly Gly Gly Gly Ser
1 5

<210> SEQ ID NO 83
<211> LENGTH: 15
<212> TYPE: PRT
<213> ORGANISM: Artificial Sequence -continued

```
<220> FEATURE:
<223> OTHER INFORMATION: isolated synthetic linker

<400> SEQUENCE: 83

Gly Gly Gly Gly Ser Gly Gly Gly Gly Ser Gly Gly Gly Gly Ser
1               5                   10                  15
```